United States Patent [19]

Demers et al.

[11] Patent Number: 5,464,865
[45] Date of Patent: Nov. 7, 1995

[54] 4-ARYL- AND 4-ARYLTHIO-5-HYDROXY-2(5H)-FURANONES AS INHIBITORS OF PHOSPHOLIPASE $A_2$

[75] Inventors: James P. Demers, New York, N.Y.; Richard B. Sulsky, Franklin Park, N.J.

[73] Assignee: Ortho Pharmaceutical Corporation, Raritan, N.J.

[21] Appl. No.: 171,725

[22] Filed: Dec. 22, 1993

[51] Int. Cl.[6] .................................................. A61K 31/34
[52] U.S. Cl. ............................ 514/473; 549/314; 549/315
[58] Field of Search ................................... 549/315, 314; 514/473

[56] References Cited

U.S. PATENT DOCUMENTS

| | | | |
|---|---|---|---|
| 4,874,782 | 10/1989 | Bonjouklian et al. | 549/313 |
| 5,037,811 | 8/1991 | Lee | 549/313 |
| 5,134,128 | 7/1992 | Lee et al. | 549/313 |
| 5,183,906 | 2/1993 | Lee et al. | 549/313 |

Primary Examiner—James H. Reamer
Attorney, Agent, or Firm—Joseph J. Brindisi; Steven P. Berman

[57] ABSTRACT

The invention provides novel 5-hydroxy-4-aryl- and 5-hydroxy-4-(arylthio)-2(5H)-furanones of the following structure:

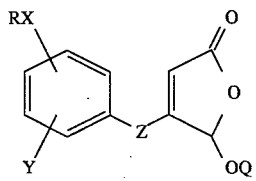

-continued

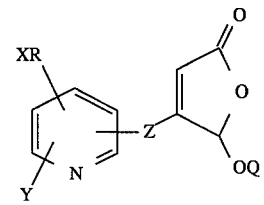

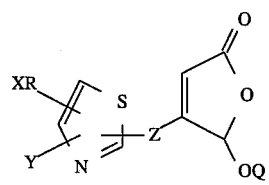

wherein R contains from about five to about twenty carbon atoms and is defined herein; X is oxygen, sulfur, $SO_2$, NH, N(lower alkyl), N(lower acyl), aminocarbonyl, carbonyl, carbonylamino, $CH_2$ or a carbon-carbon bond; Y is hydrogen, halogen, lower alkyl, nitro, alkylthio, perfluoroalkyl, hydroxy, or lower alkoxy($C_1$–$C_8$); Z is sulfur or a carbon-carbon bond; and Q is H, an alkyl of from 1–20 carbon atoms, COR', COOR', CONHR', PO(OR')2, PO(OR')R" wherein R' and R" are independently selected from the group consisting of H, an alkyl of from 1–20 carbon atoms, phenyl, and substituted phenyl and prodrugs thereof and pharmaceutically acceptable salts thereof. Pharmaceutical compositions comprising these compounds, methods of using these compounds as inhibitors of inflammation and for treating other diseases characterized by the overproduction of arachidonic acid metabolites, intermediates and methods of preparing these compounds are also provided.

18 Claims, No Drawings

4-ARYL- AND 4-ARYLTHIO-5-HYDROXY-2(5H)-FURANONES AS INHIBITORS OF PHOSPHOLIPASE A₂

FIELD OF THE INVENTION

This invention relates to novel 5-hydroxy-4-aryl- and 5-hydroxy-4-(arylthio)2(5H)-furanones. The invention also provides novel methods for the preparation of these materials, and for the preparation of 5-hydroxy-4-(heterocyclyl)-2(5H)furanones. The compounds of the invention inhibit phospholipase $A_2$, and thereby reduce arachidonic acid liberation from phospholipids. Some of the compounds also inhibit lipoxygenase. The compounds are useful as inhibitors of inflammation, and for treating other diseases characterized by the overproduction of arachidonic acid metabolites.

BACKGROUND OF THE INVENTION n

The term "phospholipase $A_2$" ($PLA_2$) refers to a large class of enzymes which cleave the sn-2 acyl group from phospholipids. The mammalian $PLA_2$ enzymes involved in inflammatory reactions primarily release arachidonic acid from cell membrane phospholipids; this arachidonic acid is further converted into prostaglandins and leukotrienes. The action of $PLA_2$ on 1-alkyl-2-acyl phospholipids leads to the production of platelet activating factor (PAF), another pro-inflammatory substance. An in vivo inhibitor of $PLA_2$, therefore, would be expected to reduce the levels of prostaglandins, leukotrienes, and PAF in tissues. A drug with this activity may offer advantages over the presently known cyclooxygenase inhibitors (aspirin, indomethacin, and other NSAIDs), and also over lipoxygenase inhibitors and PAF antagonists, in the treatment of inflammatory conditions.

The corticosteroids (hydrocortisone and its many synthetic analogues) inhibit $PLA_2$ indirectly, apparently by regulating the expression of a number of genes in mammalian cells, some of which code for $PLA_2$ modulators. The resulting anti-inflammatory effect is far superior to that of the NSAIDs, but the many side-effects of steroids prevent their routine use in long-term treatment of chronic inflammatory diseases. A direct inhibitor of $PLA_2$ would not affect gene expression, and would therefore be expected to exhibit steroid-like anti-inflammatory activity with fewer side-effects than the steroids.

A number of inhibitors of $PLA_2$ have been described including manoalide which is a natural product with anti-inflammatory activity, produced by the marine sponge *Luffariella variabilis*.

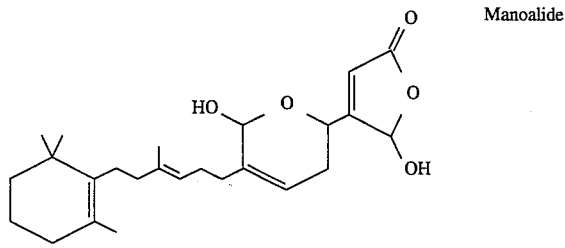

Manoalide

The isolation and structure determination of manoalide were first reported by E. D. deSilva and P. J. Scheuer in *Tetrahedron Letters*, 21, 1611 (1980). Manoalide was subsequently reported to be a potent inhibitor of $PLA_2$ by J. C. de Freitas et al., *Experientia*, 40, 864 (1984); this activity was also disclosed by R. S. Jacobs and D. J. Faulkner in U.S. Pat. No. 4,447,445. The latter patent also disclosed similar activities for seco-manoalide (a natural product) and dehydro-seco-manoalide (an artifact of isolation), which materials were first reported by de Silva and Scheuer in *Tetrahedron Letters*, 22, 3147 (1981). U.S. Pat. No. 5,037,811 discloses various furanone derivatives with anti-inflammatory activity.

It is an object of the present invention to provide novel 4-aryl or 4-arylthio-5 -hydroxy-2(5H)-furanones which are useful as $PLA_2$ inhibitors and antiinflammatory agents. As a class, 5-hydroxy-2(5H)-furanones have been known for some time, and a few 4-aryl derivatives are known. However, none of the known 4-aryl derivatives carry the RX group of the present invention, and the RX group is essential to the biological activity of the compounds of the invention.

It is an object of the present invention to provide novel methods of preparing the 4-aryl or 4-arylthio-5-hydroxy-2(5H)-furanones of the invention. Additional objects and advantages of the invention will be set forth, in part, in the description which follows and in part will be obvious from this description, or may be learned by practice of the invention. The objects and advantages of this invention are realized and obtained by means of the compositions, methods and the combinations particularly pointed out in the appended claims and their equivalents.

SUMMARY OF THE INVENTION

To achieve the objects in accordance with the purposes of the invention, as embodied and fully described herein the present invention is directed to new compounds of the following structure:

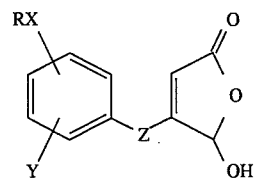

In formula 1 above: R contains from about five to about twenty carbon atoms and is selected from alkyl, acyl, cycloalkyl, aryl-alkyl, (cycloalkyl)alkyl, alkenyl, aryl-alkenyl, alkynyl, (cycloalkyl)alkynyl, (cycloalkyl)alkenyl, aryl-alkynyl or aryl groups wherein said alkyl, cycloalkyl, aryl-alkyl, (cycloalkyl)alkyl, alkenyl, aryl-alkenyl, alkynyl, (cycloalkyl)alkynyl, (cycloalkyl)alkenyl, aryl-alkynyl or aryl groups are unsubstitiuted or substituted by one or more lower alkyl groups, said cycloalkyl groups may incorporate one or more double bonds, said aryl groups may be monocyclic or fused bicyclic, and said aryl groups are unsubstituted or substituted by one or more halogen, nitro, lower alkyl, lower alkylthio, perfluoroalkyl, hydroxy, or lower alkoxy groups;

X is oxygen, sulfur, $SO_2$, NH, N(lower alkyl), N(lower acyl), aminocarbonyl, carbonyl, carbonylamino, $CH_2$ or a carbon-carbon bond;

Y is hydrogen, halogen, nitro, lower alkyl, alkylthio, perfluoroalkyl, hydroxy, or lower alkoxy; and Z is sulfur, a five- or six-membered heterocyclic ring or a carbon-carbon bond.

The group RX preferably contains from about five to about twenty carbon atoms, and as a rule the compounds will be inhibitors of phospholipase $A_2$ so long as RX is of this approximate size. The group RX is preferably non-polar and hydrophobic. As used above, the terms "lower alkyl", "lower alkenyl", "lower alkoxy", and "lower acyl" refer to groups having from one to about eight carbon atoms. The term "alkyl", used alone or in combinations such as arylalkyl, alkylthio, alkylamino, etc., refers to both branched and straight-chain alkyl groups. The term "acyl" likewise refers to both branched and straight-chain acyl groups. The term "cycloalkyl" refers to cycloalkyl groups of from three to about eight carbon atoms. The term "alkenyl" refers to both branched and straight-chain alkenyl groups, containing one or more double bonds of either cis or trans stereochemistry. The compounds of the invention contain at least one chiral center, and both the racemic form and the pure enantiomers, and any pure diastereomers resulting from the presence of other chiral centers, are included within the scope of the invention.

The invention also comprises heterocyclic compounds of the formulae:

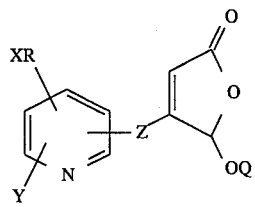

2

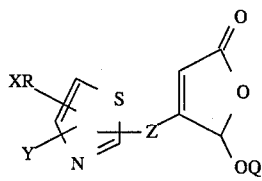

3 wherein R, X, Y, and Z are as defined above and Q is H and as otherwise defined below.

The invention also comprises prodrugs of the above in accordance with the formula:

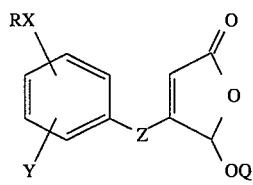

wherein Q is an alkyl of from 1–20 carbon atoms, COR', COOR', CONHR', PO(OR')2, PO(OR')R" wherein R' and R" are independently H, an alkyl of from 1–20 carbon atoms, phenyl, or substituted phenyl. These particular furanone ring substitutions and their methods of preparation are disclosed in U.S. Pat. No. 5,037,811, the entire disclosure of which is hereby incorporated herein by reference.

The invention comprises pharmaceutically acceptable salts of all the above-identified compounds and pharmaceutical compositions comprising said compounds and a pharmaceutically acceptable carrier.

The invention further comprises the use of the above compounds for the treatment of diseases mediated by, or characterized by overproduction of, arachidonic acid metabolites, especially inflammatory diseases in mammals; for the treatment of mammalian diseases that are responsive to modulation of intracellular calcium levels; and for treatment of proliferative diseases such as psoriasis.

The invention also comprises a novel method of synthesis of 5-hydroxy-2(5H)-furanones, which avoids the use of aldehydes as starting materials. This is an improvement over conventional processes since the particularly unstable arylacetaldehydes can be avoided. The method is applicable to the synthesis of 5-hydroxy-4-(heterocyclyl)-2(5H)-furanones as well. The method comprises the steps of reacting an aldehyde ketal of formula:

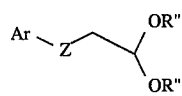

wherein R" is lower alkyl, with glyoxylic acid in the presence of a secondary amine salt to prepare compounds of formula:

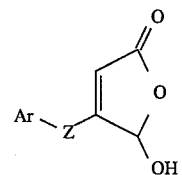

wherein Z is sulfur or a carbon-carbon bond, and wherein Ar is an optionally substituted aromatic or heterocyclic ring.

It is to be understood that both the foregoing general and the following detailed description are exemplary and explanatory only and are not intended to be restrictive of the invention as claimed.

Reference will now be made in detail to certain preferred embodiments of the invention; examples of which are illustrated below.

DETAILED DESCRIPTION OF THE INVENTION

The present invention provides structural analogues of manoalide in which the dihydropyran ring of manoalide is replaced with an aromatic ring. The dihydropyran ring of manoalide is capable of reversible opening, to generate a reactive alpha, beta-unsaturated aldehyde (R. Deems et al, *Biochim. Biophys. Acta*, 917, 258 (1987)); this characteristic is believed to be responsible for the irreversible nature of $PLA_2$ inhibition by manoalide (B. Potts et al., *J. Amer. Chem. Soc.*, 114, 5093 (1992)). The compounds of the present invention differ from manoalide because they have the advantage of reversibly inhibiting $PLA_2$ without being convertible into a reactive species, and thus can be expected to be more selective for the target enzyme, and more stable to metabolism.

The compounds of the invention are shown herein to inhibit $PLA_2$, and to inhibit TPA-induced edema in the mouse ear when applied topically.

The invention comprises compounds of the following general structure, and pharmaceutical compositions containing them:

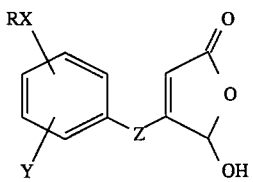

In formula 1 above: R contains from about five to about twenty carbon atoms and is selected from alkyl, acyl, cycloalkyl, aryl-alkyl, (cycloalkyl)alkyl, alkenyl, aryl-alkenyl, alkynyl, (cycloalkyl)alkynyl, (cycloalkyl)alkenyl, aryl-alkynyl or aryl groups wherein said alkyl, cycloalkyl, aryl-alkyl, (cycloalkyl)alkyl, alkenyl, aryl-alkenyl, alkynyl, (cycloalkyl)alkynyl, (cycloalkyl)alkenyl, aryl-alkynyl or aryl groups are unsubstitiuted or substituted by one or more lower alkyl groups, said cycloalkyl groups may incorporate one or more double bonds, said aryl groups may be monocyclic or fused bicyclic, and said aryl groups are unsubstituted or substituted by one or more halogen, nitro, lower alkyl, lower alkylthio, perfluoroalkyl, hydroxy, or lower alkoxy groups;

X is oxygen, sulfur, $SO_2$, NH, N(lower alkyl), N(lower acyl), aminocarbonyl, carbonyl, carbonylamino, $CH_2$ or a carbon-carbon bond;

Y is hydrogen, halogen, nitro, lower alkyl, alkylthio, perfluoroalkyl, hydroxy, or lower alkoxy; and Z is sulfur, a five- or six-membered heterocyclic ring or a carbon-carbon bond.

The group RX preferably contains from about five to about twenty carbon atoms, and as a rule the compounds will be inhibitors of phospholipase $A_2$ so long as RX is of this approximate size. The group RX is preferably non-polar and hydrophobic. As used above, the terms "lower alkyl", "lower alkenyl", "lower alkoxy", and "lower acyl" refer to groups having from one to about eight carbon atoms. The term "alkyl", used alone or in combinations such as arylalkyl, alkylthio, alkylamino, etc., refers to both branched and straight-chain alkyl groups. The term "acyl" likewise refers to both branched and straight-chain acyl groups. The term "cycloalkyl" refers to cycloalkyl groups of from three to about eight carbon atoms. The term "alkenyl" refers to both branched and straight-chain alkenyl groups, containing one or more double bonds of either cis or trans stereochemistry. The compounds of the invention contain at least one chiral center, and both the racemic form and substantially pure enantiomers, and any substantially pure diastereomers resulting from the presence of other chiral centers, are within the scope of the invention.

In preferred embodiments of the invention R is preferably from about five to about twenty carbon atoms. More particularly, the preferred compounds contain a group RX that is hydrophobic and non-polar. The intervening group X is preferably of a non-polar nature, especially preferred are oxygen, sulfur, $CH_2$, or a carboncarbon bond. The group Y is preferably a non-polar group such as hydrogen, halogen, alkoxy, alkylthio, alkyl, perfluoroalkyl, and the like.

The invention also comprises prodrugs of the above in accordance with the formula:

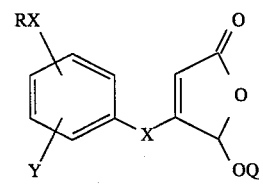

wherein Q is an alkyl of from 1–20 carbon atoms, COR', COOR', CONHR', PO(OR')2, PO(OR')R" wherein R' and R" are independently H, an alkyl of from 1–20 carbon atoms, phenyl, or substituted phenyl.

The invention comprises pharmaceutically acceptable salts of all the above-identified compounds and pharmaceutical compositions comprising said compounds and a pharmaceutically acceptable carrier.

SYNTHESIS OF THE COMPOUNDS OF THE INVENTION

The reaction of aliphatic aldehydes with glyoxylic acid to produce furanones was first disclosed by J. Bourguignon and C. Wermuth in *J. Org. Chem.*, 46, 4889 (1981). A novel feature of the method disclosed herein is in the substitution of an aldehyde acetal for an isolated aldehyde. The advantage of using this method is that the acetal 4 (Scheme 1) is slowly hydrolyzed to the corresponding aldehyde 7 by the weak acid glyoxylic acid, and the released aldehyde 7 then condenses immediately with glyoxylic acid. The concentration of 7 is thus never high enough to permit self-condensation or polymerization. Furthermore, the difficulties associated with preparing, purifying, and storing unstable aldehydes, especially the arylacetaldehydes required for the com. pounds of this invention, are eliminated.

The compounds of the invention where Z is a carbon-carbon bond are prepared by condensation of glyoxylic acid with the appropriate aryl acetaldehyde, or with the enol ether or dialkyl ketal thereof, as shown in Scheme 1.

SCHEME 1

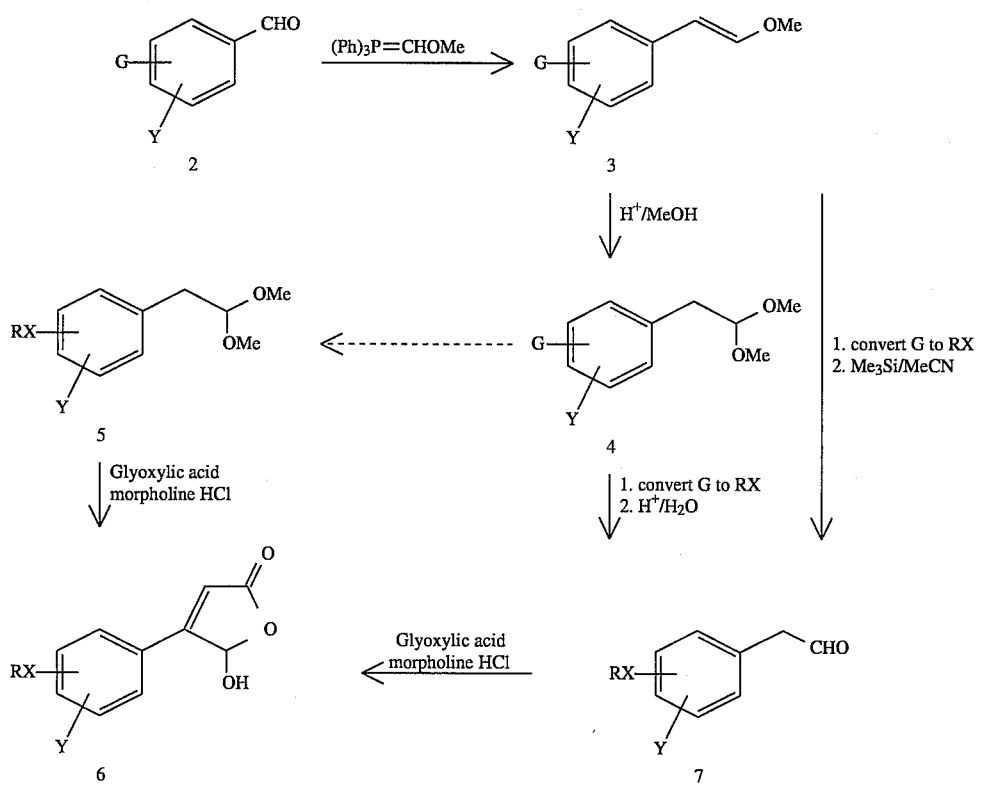

In general, a substituted benzaldehyde 2 is converted by known methods into the homologated aldehyde 7, or the functionally equivalent acetal 4 or enol ether 3. In the examples below, this is accomplished by treatment of 2 with methoxymethyl triphenylphosphonium chloride (or bromide) in the presence of a strong base, such as potassium t-butoxide, in a suitable solvent such as THF. The resulting enol ether 3 is then treated with a catalytic amount of acid in an alcohol such as methanol to generate the acetal 4, or is treated with a silyl halide such as iodotrimethylsilane to generate the aldehyde 7. Acetals analogous to 4, but derived from other lower alchohols, or a cyclic acetal derived from a lower diol, are of equal utility in the following reactions. The acetal 4 may be hydrolyzed with aqueous acid, generating the aldehyde 7, or may be reacted directly with glyoxylic acid to generate 6. The acetals 4 are much more stable to storage and to chemical manipulation than the enol ethers 3 or the corresponding aryl acetaldehydes 7, and are the preferred intermediates for conversion of group G into group RX. The acetals 4 are also the preferred intermediates for condensation with glyoxylic acid for the preparation of the desired butenolides 6.

The group G in structures 2, 3, and 4 may be the desired final substituent RX, or it may be a reactive functional group capable of being transformed into the desired group RX. For example, the groups G=triflate or G=iodide can be converted to alkynyl groups by treatment with a terminal alkyne in the presence of a palladium catalyst, or the group G=HC≡C can be arylated by treatment with an aryl iodide or aryl triflate in the presence of the same catalyst. The groups G=OH or G=SH can be alkylated, and the group G=NH2 can be alkylated, acylated or sulfonylated, to generate the acetals 5 where X is —O—, —S—, NR'—, —CONH—, or —SO2NH—. The group G =Br can be exchanged for the group G=Li, and a variety of electrophiles added to the resulting aryllithium. The methods for these conversions are all well-known in the art. Due to the chemical stability of the acetal group of 4 relative to the aldehydes 2 or 7 or the enol ether 3, it is usually desirable to conduct the transformation of G into RX at the acetal stage 4. In applying the teachings of this invention to compounds not specifically exemplified in this disclosure, the practitioner will choose an appropriate group G and will select the method of conversion of G into the desired group RX from the known art.

The conversion of G to RX may optionally be carried out at an earlier stage, if the reaction conditions are compatible with an aldehyde or enol ether, or the benzaldehyde 2 may be synthesized with the group RX already in place. The preferred method will be dependent on the nature and availability of the group R; those skilled in the art will appreciate that if R is difficult to prepare or is otherwise valuable, the conversion of G to RX will be carried out as late in the synthesis as possible. Specific examples of these options, and of various transformations of precursor groups G into target groups RX, are to be found in the examples below.

Conversion of either 4 or 7 into the butenolide 6 is carried out by condensation with glyoxylic acid in the presence of a secondary amine salt, in an inert solvent. The salt is preferably morpholine hydrochloride, and the solvent is preferably a water-miscible solvent, such as 1,4-dioxane, containing enough water to dissolve the amine salt. The acetal 4 is preferred to either 3 or 7 for this reaction.

For the preparation of 5-hydroxy-4-(heterocyclyl)-2(5H)-furanones, the chemistry of Scheme 1 is employed, but with a heterocyclic ring in place of the benzene ring.

The synthesis of the furanones 1 where Z is sulfur is carried out in similar fashion, as shown in Scheme 2.

SCHEME 2

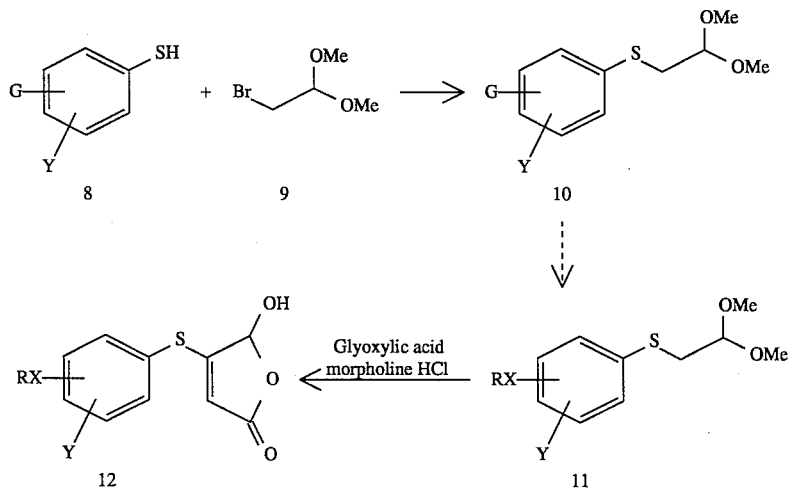

In this case, a substituted thiophenol 8 is alkylated with 1-bromo-2,2-dimethoxyethane 9 in the presence of a base, for example potassium carbonate, in a suitable solvent such as DMF. The resulting thioether 10 is converted (if necessary) to the thioether 11 having the desired group RX, and 11 is taken on to the furanone as described above. The considerations discussed above regarding the identifies of G and RX, and the timing of the conversion of G to RX, apply to the synthesis outlined in Scheme 2 as well. It is anticipated that the chemistry of Scheme 2 will be applicable to the synthesis of 4-((heterocyclyl)thio)-5-hydroxy-2(5H)-furanones, by the simple substitution of a mercapto-heterocycle for the thiophenol 8.

One skilled in the art of medicinal chemistry will appreciate that pro-drug esters, ethers, carbonates, carbamates, and phosphate esters of the furanone 5-hydroxy group could be prepared, in order to modify the absorption, tissue distribution, and metabolism of the compounds of this invention, and such prodrugs are contemplated and intended to be within the scope of this invention.

Representative examples and methods of preparation of such prodrugs are disclosed in U.S. Pat. No. 5,037,811 issued Aug. 6, 1991, the contents of which have been incorporated herein by reference.

The invention will now be illustrated by examples. The following examples describe the invention in greater particularity and are illustrative but not limiting of the scope of the present invention. In conjunction with the detailed and general description above, the examples provide further understanding of the present invention and outline a process for producing the compounds of the invention. The following examples represent preferred embodiments of the compounds, compositions, processes and methods of the invention for satisfying the stated objects of the invention.

EXAMPLES

The following processes and procedures for preparing the compounds of the present invention are identified in the reaction schemes illustrated above. The schemes and the specific examples below describe with particularity the various chemical reactions and procedures utilized. Any methods, starting materials or reagents which are not particularly described are those which are known and available to those skilled in the art.

The examples below are provided only to illustrate the invention, and the limited number of examples is not intended to limit the scope of the invention. Purification by chromatography refers to column chromatography on commercially available silica gel adsorbent. Drying of organic solutions may be accomplished by stirring with anhydrous magnesium sulfate and filtering.

Example 1

5-Hydroxy-4-(4-octyloxyphenyl)-2(5H)furanone

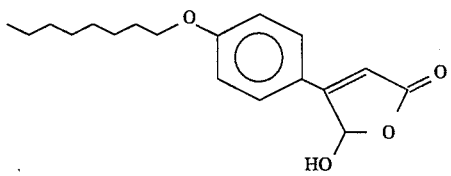

A. Preparation of aldehyde enol ether.

Sodium hydride (4.2 g of 60% dispersion in oil) is added to a solution of 4-hydroxybenzaldehyde (12.2 g) in dimethylformamide. The mixture is stirred for 30 min, and 1-bromooctane (18 ml) is added. The reaction mixture is stirred at 90° for five hours, cooled, and the solvent removed in vacuo. The residue is shaken with water, and extracted with three portions of hexane. The hexane extracts are dried, concentrated, and distilled in vacuo to provide 20.3 g of 4-octyloxybenzaldehyde.

Potassium t-butoxide (1.9 g) is added to a slurry of methoxymethyl triphenylphosphonium chloride (6.17 g) and 18-Crown-6 (100 mg) in dry THF (40 ml). The mixture is stirred for 5 min, cooled to 15°, and a solution of 4-octyloxybenzaldehyde (3.52 g) in THF (5 ml) is added dropwise. The reaction mixture is stirred at room temperature for 20 min, diluted with 250 ml hexane, and the resulting mixture filtered through a pad of diatomaceous earth. Evaporation of the filtrate leaves crude 1-(2-methoxyethenyl)-4-(octyloxy)benzene as a mixture of cis and trans isomers, containing about 15 mol % triphenylphosphine oxide. The crude material may be used as is, or may be chromatographed with 1:1 hexanedichloromethane.

B. Preparation of arylacetaldehyde.

A solution of 1-(2-methoxyethenyl)-4-(octyloxy)benzene (3.67 g) and methanesulfonic acid (0.5 ml) in methanol (30 ml) is refluxed for 30 min, cooled, and neutralized with 1.0N aqueous sodium bicarbonate (10 ml). The mixture is evaporated in vacuo, and the residue dissolved in ether, dried with sodium sulfate, filtered, and evaporated to leave 1-(2,2-dimethoxyethyl)-4-(octyloxy)benzene as a colorless oil. This acetal may be used directly in step C below (as in example 2). Alternatively, the acetal is dissolved in a 1:1 mixture of THF and 3N hydrochloric acid, refluxed for one hour, and cooled. The mixture is extracted with dichloromethane, and without drying the dichloromethane extracts are concentrated to provide crude 4-(octyloxy)phenylacetaldehyde as an oil.

C. Preparation of furanone.

Water (ca. 5 ml) is added dropwise to a slurry of morpholine hydrochloride (2.58 g) and glyoxylic acid hydrate (1.93 g) in dioxane (18 ml) until the solids dissolve. The solution is stirred for one hour, 4-(octyloxy)phenylacetaldehyde is added, and the mixture is stirred at reflux for 24 hr. The mixture is cooled, diluted with water, and extracted with dichloromethane. The extracts are dried, concentrated, and then chromatographed with 5% ether in dichloromethane.

The title product is obtained as a white solid, mp 81°–82° (1.83 g, 40% overall from the enol ether).

Example 2

5-Hydroxy-4-(2-chloro-4-octyloxyphenyl)-2(5H)furanone

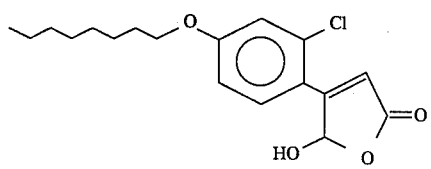

By the method of example 1 above, but condensing the intermediate 2-chloro-1-(2,2-dimethoxyethyl)-4-(octyloxy)benzene directly with glyoxylic acid, 2-chloro-4-hydroxybenzaldehyde is converted into the title compound, obtained as a white solid, mp 75°–77°.

Example 3

5-Hydroxy-4-(3-octyloxyphenyl)-2(5H)furanone

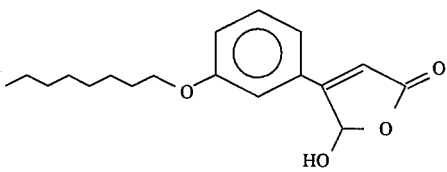

By the method of example 2 above, 3-hydroxybenzaldehyde is converted into the title compound, obtained as a white solid, mp 95°–96°.

Example 4

5-Hydroxy-4-(3-chloro-4-octyloxyphenyl)-2(5H)furanone

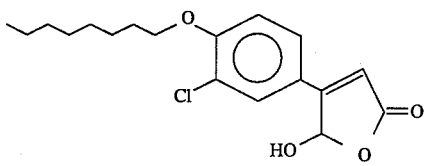

By the method of example 2 above, 3-chloro-4-hydroxybenzaldehyde is converted into the title compound, obtained as a pale yellow solid, mp 108°–110°.

Example 5

5-Hydroxy-4-(2-methoxy-4-octyloxyphenyl)-2(5H)furanone

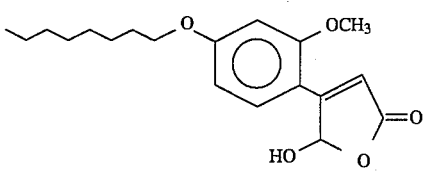

By the method of example 2 above, 2-methoxy-4-hydroxybenzaldehyde is converted into the title compound, obtained as a white solid, mp 117°–119°.

Example 6

5-Hydroxy-4-(3-methoxy-4-octyloxyphenyl)-2(5H)furanone

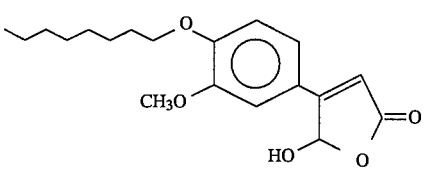

By the method of example 2 above, 3-methoxy-4-hydroxybenzaldehyde is converted into the title compound, obtained as a white solid, mp 73°–74°.

Example 7

5-Hydroxy-4-(3-nitro-4-octyloxyphenyl)-2(5H)furanone

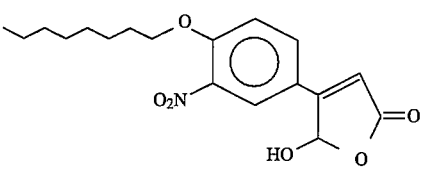

By the method of example 2 above, 3-nitro-4-hydroxybenzaldehyde is converted into the title compound, obtained as a white solid, mp 108°–110°.

Example 8

5-Hydroxy-4-(2-octyloxyphenyl)-2(5H)furanone

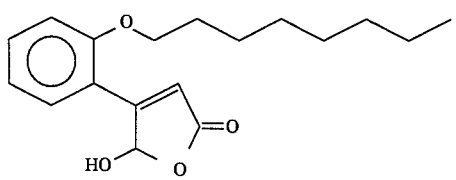

By the method of example 2 above, 2-hydroxybenzaldehyde is converted into the title compound, obtained as a white solid, mp 119°–121°.

Example 9

5-Hydroxy-4-(3-acetamido-4-octyloxyphenyl)-2(5H)furanone

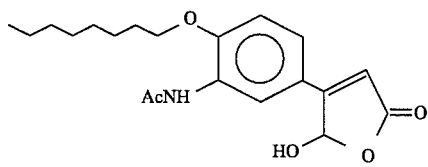

By the method of example 1 above, 3-nitro-4-hydroxybenzaldehyde is converted into 1-(2,2-dimethoxyethyl)-3-nitro-4-octyloxybenzene. This material (1.83 g) is dissolved in ethanol (20 ml) and to the solution is added ammonium formate (3.5 g) and palladium black (0.30 g), and the mixture is stirred for 30 min. The mixture is filtered through diatomaceous earth and evaporated to dryness in vacuo. The residue is partitioned between water and dichloromethane, and the organic phase is dried over magnesium sulfate, filtered, and concentrated to give 1-(2,2-dimethoxyethyl)-3-amino-4-octyloxybenzene as an orange oil (1.64 g, 98%).

This material is dissolved in dichloromethane (15 ml), and triethylamine (0.8 ml), 4-(dimethylamino)pyridine (0.1 g) and acetic anhydride (0.52 ml) are added. The mixture is stirred for 16 hr, the solvent is removed in vacuo, and the residue is dissolved in ether and washed successively with 1.0N sodium bicarbonate, 10% w/v citric acid, and again with 1.0N bicarbonate. The solution is then dried over magnesium sulfate, filtered, and evaporated to leave 1-(2,2-dimethoxyethyl)-3-acetamido-4-octyloxybenzene as a light yellow oil.

By the method of example 2, this material is condensed directly with glyoxylic acid to provide the title compound as a light yellow solid, mp 168°–169°

Example 10

5-Hydroxy-4-[4-(3-phenylpropyloxy)phenyl]-2(5H)furanone

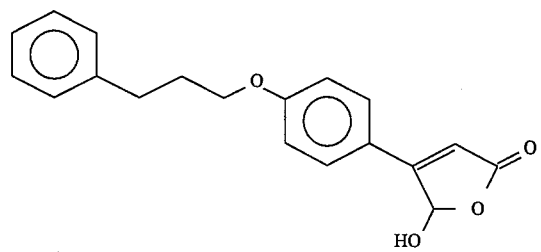

By the method of example 1 above, 4-hydroxybenzaldehyde and (3-bromopropyl)benzene are converted into the title compound, obtained as a tan solid, mp 125°–127°.

Example 11

5-Hydroxy-4-[(3-allyloxy)phenyl]-2(5H)furanone

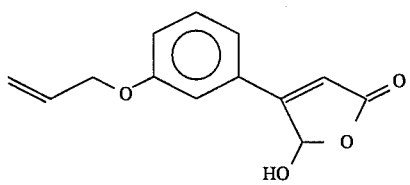

By the method of example 1 above, 3-hydroxybenzaldehyde and allyl bromide are converted into the title compound, obtained as a white solid, mp 103°–105°.

Example 12

5-Hydroxy-4-[4-(2-(2-naphthyloxy)ethoxy)phenyl]-2(5H)furanone

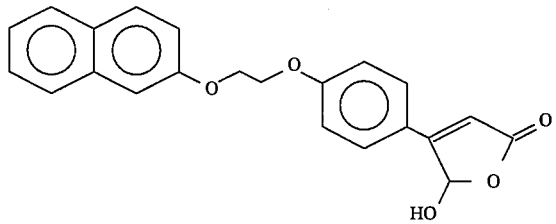

By the method of example 1 above, 4-hydroxybenzaldehyde and 2-(2-bromoethoxy)naphthalene are converted into the title compound, obtained as a white solid, mp 206°–208°.

Example 13

5-Hydroxy-4-[4-(6-(2-naphthyloxy)hexyloxy)phenyl]-2(5H)furanone

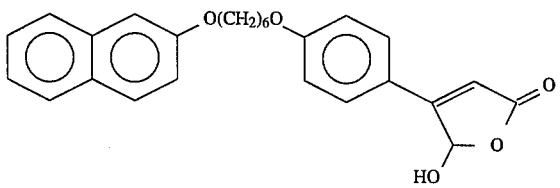

Ethyl 6-bromohexanoate and the sodium salt of 2-naphthol are reacted in DMF at 70° to provide ethyl 6-(2- naphthyloxy)hexanoate, which after the usual workup is reduced with lithium aluminum hydride in THF to provide 6-(2-naphthyloxy)hexanol.

Mitsunobu coupling is carried out as follows: 4-hydroxybenzaldehyde (0.92 g), 6-(2-naphthyloxy)hexanol (1.83 g), and triphenylphosphine (1.97 g) are dissolved in THF (25 ml) and cooled to 15°. Diethyl azodicarboxylate (1.2 ml) is added dropwise, and the mixture stirred at room temperature for 60 hrs. The reaction mixture is diluted with hexane and filtered to remove solids. The filtrate is concentrated and chromatographed with 25% v/v hexane in dichloromethane to provide 4-[6-(2-naphthyloxy)hexyloxy] benzaldehyde (1.5 g) as a white solid.

By the method of example 1 above, 4-[6-(2-naphthyloxy)hexyloxy] benzaldehyde is converted into the title compound, obtained as a white solid, mp 177°–179°.

Example 14

(E)-5-Hydroxy-4-(4-(2-methyl-7-(2,6,6-trimethyl-1-cyclohexen-1-yl)-2-heptenyloxy)phenyl)-2 (5H)-furanone

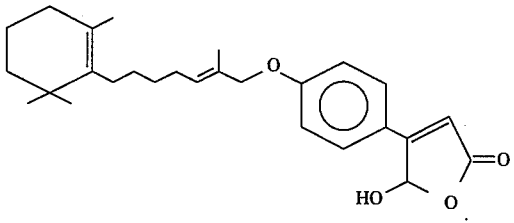

A. 4-[(2,2-Dimethoxy)ethyl]phenol.

Triethylamine (42 ml) is added dropwise to a stirred solution of 4-hydroxybenzaldehyde (33.5 g) and chlorotrimethylsilane (42 ml) in ether (300 ml). After 15 min, the mixture is filtered through diatomaceous earth and the filtrate is concentrated and distilled in vacuo, providing 4-(trimethylsilyoxy)benzaldehyde as a colorless oil (43 g). This material is reacted with methoxymethyl triphenylphosphonium chloride and potassium tert-butoxide in THF, using the procedure described in Example 1 (A) above, to provide 1-(2-methoxyethenyl)-4-(trimethylsiloxy)benzene (35%) as a colorless oil after distillation in vacuo, as a mixture of (E) and (Z) isomers. This material (3.0 g) is dissolved in methanol (30 ml) containing methanesulfonic acid (0.4 ml), and the solution is refluxed for 3 hr. Sodium bicarbonate (8 ml of 1.0N solution) is added, and the mixture is concentrated in vacuo. The residue is taken up in ethyl acetate, dried, and concentrated to provide 4-[(2,2-dimethoxy)ethyl] phenol as a pale red oil (2.4 g).

B. (2E)-2-Methyl-7-(2,6,6-trimethyl-1-cyclohexen-1-yl)-2-heptenol.

Commercially available 2,6,6-trimethyl-1-cyclohexene-1-acetaldehyde is chain-extended by Wittig reaction with commercially available 2-(1,3-dioxan-2-yl)ethyl triphenylphosphonium bromide as follows: To a stirred suspension of the phosphonium salt (20.4 g) in THF (30 ml) is added HMPA (30 ml). The mixture is cooled to −70° under nitrogen and n-butyllithium (17.5 ml of 2.5M solution in hexane) is added dropwise. After 30 minutes the aldehyde (6.65 g in 10 ml THF) is added and the mixture is allowed to warm slowly to room temperature. Water and hexane are added, the organic phase is evaporated and the residue chromatographed with 40% dichloromethane in hexane to provide crude (mostly cis) 2-[4-(2,6,6-trimethyl-1-cyclohexen-1-yl)-2-butenyl]-1,3-dioxane as a colorless oil (5.26 g). This material is hydrogenated in ethanol over a 5% Pd/BaSO4 catalyst for 18 hr under 40 psi hydrogen. Filtration and evaporation provide crude 2-[4-(2,6,6-trimethyl-1-cyclohexen-1-yl)butyl]-1,3-dioxane as a colorless oil. This is hydrolyzed with acid in refluxing 1:1 dioxane-water to provide 5-(2,6,6-trimethyl-1-cyclohexen-1-yl)pentanal as a colorless oil.

To a stirred solution of triethyl 2-phosphonopropionate (4.2 g) in THF (25 ml) under nitrogen is added sodium hydride (0.69 g of 60% dispersion in oil). After 30 minutes, 5-(2,6,6-trimethyl-1-cyclohexen-1-yl)pentanal (3.09 g) is added, and the mixture is stirred at reflux for16 hr. The reaction is cooled, poured into aqueous sodium bicarbonate, and extracted with ether. The extracts are concentrated and chromatographed with 30% dichloromethane in hexane to provide (2E)-2-methyl-7-(2,6,6-trimethyl-1-cyclohexen-1-yl)-2-heptenoic add ethyl ester as a colorless oil (2.4 g). This material (2.09 g) is reacted with diisobutylaluminum hydride (10 ml of 1.5M toluene solution) in toluene (20 ml) at −20°, stirred at 0° for 3 hr, then stirred for 16 hr with 1.0N sodium hydroxide solution. The mixture is extracted with ether, and the organic phase is concentrated and chromatographed with dichloromethane to provide 1.6 g of (2E)-2-methyl-7-(2,6,6-trimethyl-1-cyclohexen-1-yl)-2-heptenol as a colorless oil.

C. (E)-5-Hydroxy-4-(4-(-2-methyl-7-(2,6,6-trimethyl-1-cyclohexen-1-yl)-2-heptenyloxy)phenyl)-2(5H)-furanone.

(2E)-2-Methyl-7-(2,6,6-trimethyl-1-cyclohexen-1-yl)-2-heptenol (1.5 g), 4-(( 2,2-dimethoxy)ethyl)phenol (1.1 g) and triphenylphosphine (1.59 g) are dissolved in THF (10 ml) and the solution cooled to 0°. Diethyl azodicarboxylate (1.05 ml, in 9 ml THF) is added dropwise with stirring, and the mixture is allowed to warm to room temperature and stirred overnight. The reaction mixture is concentrated and the residue is chromatographed with dichloromethane to provide 4-((2,2- dimethoxy)ethyl)-1-((2E)-2-methyl-7-(2,6,6-trimethyl- 1-cyclohexen-1-yl)-2-heptenyloxy)benzene as a pale yellow oil (2.27 g). This material is reacted with glyoxylic acid and morpholine hydrochloride by the method of Example 2 above, purified by chromatography with 7% ether in dichloromethane, and recrystallized from hexane-dichloromethane to provide the title compound as a white solid, mp 119°–121° (1.0 g).

Example 15

(E)-5-Hydroxy-4-(4-(2-methyl-5-(2,6,6-trimethyl-1-cyclohexen-1-yl)-2-pentenyloxy)phenyl)-2(5H)-furanone

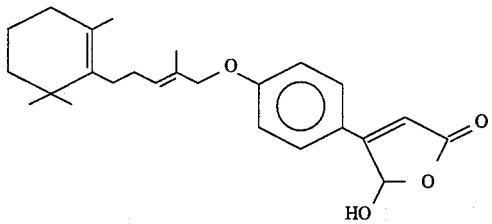

A. (2E)-2-Methyl-5-(2,6,6-trimethyl-1-cyclohexen-1-yl)-2-pentenol.

2,6,6-Trimethyl-1-cyclohexene-1-acetaldehyde is reacted with methoxymethyl triphenylphosphonium chloride in the presence of potassium tert-butoxide, followed by conversion to the dimethyl acetal and subsequent hydrolysis, as described in Example 1 above, to provide 3-(2,6,6-trimethyl-1-cyclohexen-1yl)propanal (80% yield) as a colorless oil after distillation in vacuo. This material (6.8 g) is reacted with triethyl 2-phosphonopropionate (10.6 ml) by the method of example 14(B) above, to provide 6.58 g (2E)-2-methyl-5-(2,6,6-trimethyl-1 -cyclohexen-1-yl)-2-pentenoic acid ethyl ester as a colorless oil after chromatography. This ester is reduced with diisobutylaluminum hydride by the method described in example 14(B) above, to provide (2E)-2-methyl-5-(2,6,6-trimethyl-1-cyclohexen-1-yl)-2-pentenol as a colorless oil (93%) after chromatography.

B. This alcohol is reacted with 4-((2,2-dimethoxy)ethyl)phenol in the presence of triphenylphosphine and diethyl azodicarboxylate, by the method described in example 14(C) above, to provide 4-((2,2-dimethoxy)ethyl)-1-((2E)-2-methyl-5-(2,6,6 -trimethyl-1-cyclohexen-1-yl)-2-pentenyloxy)benzene as a colorless oil (51%) after chromatography. This acetal (2.0 g) is dissolved in THF (10 ml), and water (5 ml) and 85% phosphoric acid (1.0 ml) are added. The mixture is refluxed under nitrogen for 24 hr, diluted with water, and extracted with dichloromethane. The organic extract is dried, and concentrated to provide 4-((2E)-2-methyl-5-(2,6,6-trimethyl-1 -cyclohexen-1-yl)-2-pentenyloxy)phenylacetaldehyde (1.62 g) as a colorless oil. By the method described in example 1 (C) above, this aldehyde is condensed with glyoxylic acid to provide the title compound (1.21 g, 66%) as a white solid, mp 102°–103° , after recrystallization from hexane-dichloromethane.

Example 16

(E)-5-Hydroxy-4-(4-(2-methyl-4-(2,6,6-trimethyl-1-cyclohexen-1 -yl)-2-butenyloxy)phenyl)-2 ( 5H)-furanone

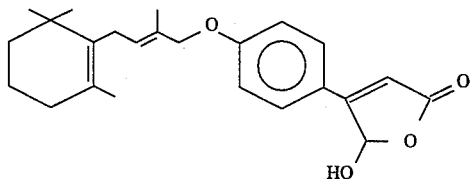

By the method of example 13 above, 4-hydroxybenzaldehyde (12.0 g) and (2E)-2-methyl-4-(2,6,6-trimethyl-1-cyclohexen-1-yl)-2-butenol (*Chem. Abstr.,* 94, 65904h) (20.5 g) are coupled with triphenylphosphine and diethyl azodicarboxylate to provide 4-((2E)-2-methyl-4-(2,6,6-trimethyl-1-cyclohexen-1-yl)-2-butenyloxy)benzaldehyde (15.9 g, 50%) as a colorless oil after chromatography. By the method of example 2 above, this is converted into the title compound, mp 136°–137° after recrystallization from hexane-dichloromethane.

Example 17

(E)-5-Hydroxy-4-(3-(2-methyl-4-(2,6,6-trimethyl-1-cyclohexen-1 -yl)-2-butenyloxy)phenyl)-2(5H)-furanone

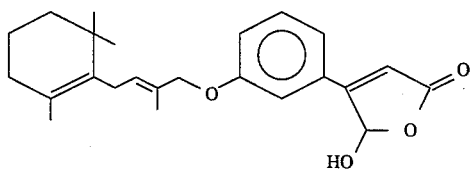

By the method of example 16 above, but using 3-hydroxybenzaldehyde, the title compound is prepared, mp 118°–119°.

Example 18

(E)-5-Hydroxy-4-(4-(2-methyl-4-(2,6,6-trimethyl-1-cyclohexen-1 -yl)-2-butenylthio)phenyl)-2(5H)-furanone

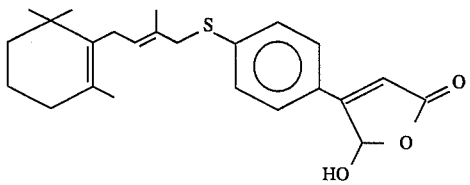

To a solution of (2E)-2-methyl-4-(2,6,6-trimethyl-1-cyclohexen-1-yl)-2-butenol (*Chem. Abstr.,* 94, 65904 h) (4.15 g) and tetrabromomethane (7.0 g) in dichloromethane (40 ml) is added over 20 min a solution of triphenylphosphine (5.51 g) in dichloromethane (30 ml). The mixture is stirred overnight under nitrogen, the solvent is removed, and the residue is triturated with hexane. The mixture is filtered, and the filtrate concentrated in vacuo to provide (2E)-1-bromo-2-methyl-4-(2,6,6-trimethyl-1-cyclohexen-1-yl)-2-butene (5.25 g) as an orange oil.

To a solution of 4-bromothiophenol (1.89 g) in THF (25 ml) is added a 60% dispersion of sodium hydride (0.44 g). The mixture is stirred under nitrogen until gas evolution ceases, and then cooled to −78° . To avoid reaction of the generated 1-bromobutane with the thiolate anion, the temperature in the subsequent reactions must be kept below −60°. A 2.5M solution of n-butyllithium in hexane (4.1 ml) is added dropwise with stirring, and the mixture stirred 20 minutes at −78°. To the resulting suspension of sodium 4-1lithiothiophenolate is slowly added DMF (0.9 ml, in 2 ml THF), and after 10 minutes the bromide prepared above is added. The mixture is stirred while being allowed to warm slowly to −20% at which point it is poured into 10% aqueous citric acid. The organic materials are extracted into ether, and the ether extracts are dried over magnesium sulfate, filtered, and evaporated. Chromatography with 1:1 dichloromethane-hexane provides 4-( (2E)-2-methyl-4-(2,6,6-trimethyl-1-cyclohexen-1-yl)-2-butenylthio)benzaldehyde (0.38 g) as a colorless oil.

By the method of example 2 above, this aldehyde is converted to the title compound, mp 115°–117°.

Example 19

5-Hydroxy-4-(4-(octylthio)phenyl)-2(5H)furanone

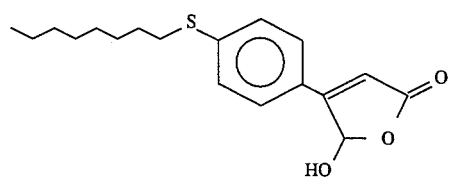

By the method of example 18 above, but using two equivalents of t-butyllithium for the transmetallation, and 1-bromooctane for the alkylation, the title compound is prepared, mp 91°–92°.

Example 20

5-Hydroxy-4-(3-(1-oxooctylamino)phenyl)-2(5H)furanone

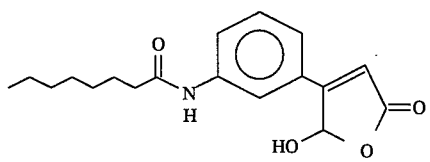

By the method outlined in example 9 above, 3-(2,2-dimethoxyethyl)aniline is prepared from 3-nitrobenzaldehyde. To a solution of this material (2.13 g) in dichloromethane (25 ml) is added triethylamine (1.7 ml). The solution is cooled in an ice bath, and octanoyl chloride (2.0 ml) is added dropwise with stirring. After 10 min, the solvent is removed in vacuo and the residue is taken up in ether, filtered, and washed with aqueous sodium bicarbonate. The solution is dried, filtered, and concentrated to leave N-(3-(2,2-dimethoxyethyl)phenyl)octanamide (3.4 g) as a light brown oil. By the method of example 2 above, this is converted into the title compound, mp 128°–130° after recrystallization from dichloromethane.

Example 21

5-Hydroxy-4-(4-(1-oxooctylamino)phenyl)-2(5H)furanone

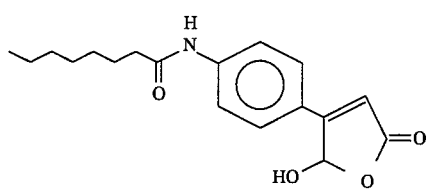

By the method of example 20 above, 4-nitrobenzaldehyde is converted into the title compound, mp 119°–121° after recrystallization from ethyl acetate-hexane.

Example 22

5-Hydroxy-4-(4-octylsulfonyl)phenyl-2(5H)furanone

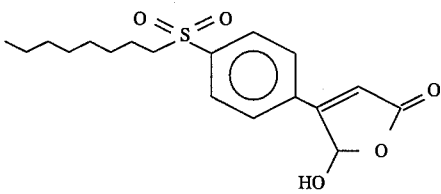

1-(2,2-Dimethoxyethyl)-4-(octylthio)benzene, prepared as in example 19 above, (1.28 g) is added dropwise to a stirred mixture of 3-chloroperbenzoic acid (2.12 g of 80% pure material) in dichloromethane (25 ml) and sodium bicarbonate (1.0 g) in water 1.3 ml). After 30 min, the reaction mixture is diluted with ether (100 ml) and washed successively with 1.0N sodium hydroxide, water, and brine. The ether solution is then dried, filtered, and evaporated to leave 1-(2,2-dimethoxyethyl)-4-(octylsulfonyl)benzene (1.36 g) as a colorless oil. By the method of example 2 above, this is converted into the title compound, mp 179°–181° after recrystallization from ethyl acetate-hexane.

Example 23

(E)-5-Hydroxy-4-(4-(3,7-dimethyl-2,6-octadienyl)thio)phenyl-2(5H)furanone

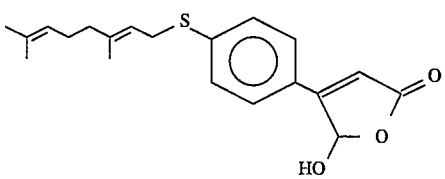

By the method of example 18 above, 4-bromothiophenol is metallated, formylated and S-alkylated with geranyl bromide. (As a consequence of the formation of bromobutane during the transmetallation with n-butyllithium, approximately 10% of the starting material is S-butylated as well. The S-butyl impurity is carried along through the rest of the synthesis.

The crude product is converted, as in Example 18, into the title compound, mp 88°–89° after chromatography with 2% ethyl ether in dichloromethane and recrystallization from dichloromethane-hexane.

Example 24

5-Hydroxy-4-(4-(butylthio)phenyl)-2(5H)furanone

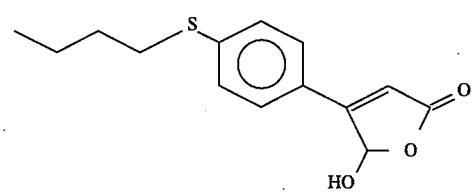

During the chromatographic purification of example 23 above, the title compound is isolated, mp 85°–86° after recrystallization from dichloromethanehexane.

Example 25

5-Hydroxy-4-(4-(N-acetyl-N-octylamino)phenyl)-2(5H)furanone

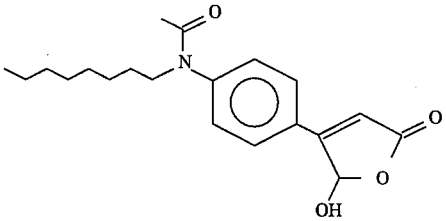

N-(4-(2,2-dimethoxyethyl)phenyl)octanamide (1.11 g, prepared as in example 21) is reduced with lithium aluminum hydride (1.4 equivalents) in refluxing THF (15 ml) to provide 1-(2,2-dimethoxyethyl)-4-(octylamino)benzene as a pale yellow oil after the usual work-up. This material (0.96 g) is dissolved in dichloromethane (10 ml) and treated with acetic anhydride (0.32 ml), triethylamine (0.5 ml) and DMAP (50 mg). The mixture is stirred at room temperature for 4 hr, then washed in turn with 10% aqueous citric acid and saturated sodium bicarbonate. The organic solution is dried, filtered, and concentrated to provide N-(4-(2,2

-dimethoxyethyl)phenyl)-N-octylacetamide as a colorless oil (1.05 g). This is condensed with glyoxylic acid by the method of example 2 above, to provide the title compound, mp 103°–105° after recrystallization from dichloromethane-hexane.

Example 26

(E)-5-Hydroxy-4-(4-(4-methyl-6-(2,6,6-trimethyl-1-cyclohexen-1- yl)-4-hexenyloxy)phenyl)-2(5H)-furanone

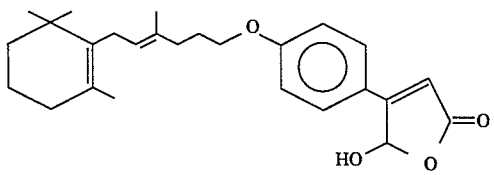

A solution of the dilithium salt of acetic acid dianion is prepared by addition of acetic acid (0.85 ml in 2 ml THF) to a solution of lithium diisopropylamide (from 4.5 ml of diisopropylamine and 12.5 ml of 2.5M n-butyllithium) in 50 ml THF at 0°. Hexamethylphosphoric triamide (8.7 ml) is added, followed by (2E)-1-bromo-2 -methyl-4-(2,6,6-trimethyl-1-cyclohexen-1-yl)-2-butene (4.0 g, prepared as in example 18, in 5 ml THF). The mixture is warmed to room temperature and stirred overnight. After quenching with 1.0N HCl, the mixture is extracted with ether, and the ether extracts washed once with water. The ether solution is then extracted with 1.0N NaOH, and the aqueous extract is acidified with HCl. The acidified solution is extracted with ether, and the ether extract is dried, filtered, and concentrated to provide (4E)-4-methyl-6-(2,6,6-trimethyl-1-cyclohexen-1-yl)-4-hexenoic acid as an orange oil. (1.3 g, 35%). This material is reduced with lithium aluminum hydride in refluxing THF in the usual fashion, to provide (4E)-4-methyl-6-(2,6,6-trimethyl-1 -cyclohexen-1-yl)-4-hexen-1-ol (1.1 g) as a colorless oil.

This hexenol (520 mg) is coupled with 4-((2,2-dimethoxy)ethyl)phenol in the presence of triphenylphosphine and diethyl azodicarboxylate, by the method described in example 14(C) above, to provide 4-((2,2-dimethoxy)ethyl)-1-((4E)-4 -methyl-6-(2,6,6-trimethyl-1-cyclohexen-1-yl)-4-hexenyloxy)benzene as a yellow oil (660 mg, 75%) after chromatography with dichloromethane. The product is condensed with glyoxylic acid by the method of example 2, to provide the title compound, mp 115°–117° after recrystallization from aqueous ethanol.

Example 27

5-Hydroxy-4-(4-(7-(2,6,6-trimethyl-1-cyclohexen-1-30 yl)heptyloxy)phenyl)-2(5H)-furanone

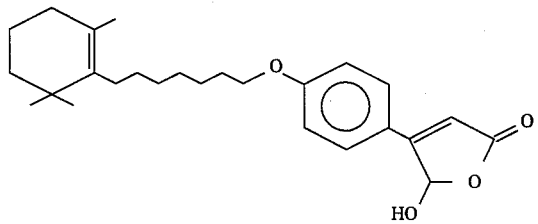

A commercial 2.5M solution of n-butyllithium in hexane (4.1 ml) is cooled to −20°. To this solution is added ((2,6,6-trimethyl-1-cyclohexen-1-yl)methyl)sulfonyl)benzene (Japanese patent 2009856 (1991), Chem. Abstr. 113, 23190) (2.78 g) in THF (20 ml) and HMPA (5 ml). After 30 min, the solution is cooled to −78°, and ethyl 6-bromohexanoate (2.36 g) is added. After an additional two hours at −78°, the mixture is allowed to warm to room temperature and stirred overnight. The mixture is quenched with 10% citric acid, and extracted with 1:1 ether-hexane. The extracts are concentrated and the residue is chromatographed with hexanedichloromethane to provide 7-(phenylsulfonyl)-7-(2, 6,6-trimethyl-1-cyclohexen-1-yl)heptanoic acid ethyl ester as a colorless oil (2.8 g, 67%). This material is reduced with lithium aluminum hydride in THF in the usual fashion to provide 7-(phenylsulfonyl)-7-(2,6,6-trimethyl-1-cyclohexen-1-yl)-1-heptanol as a colorless oil (2.44 g, 97%). This material is dissolved in diethylamine (20 ml) at 0° in a flask equipped with a mechanical stirrer, and lithium metal (0.3 g) is added. The resulting viscous mixture is stirred for two hours, quenched with water, and extracted with 1:1 hexane-ether. The extracts are concentrated and the residue chromatographed with 4:1 dichloromethane-hexane, to provide 7-(2,6,6-trimethyl-1-cyclohexen-1-yl)-1-heptanol as a colorless oil (0.77g, 50%).

This material is coupled with 4-((2,2-dimethoxy)ethyl)phenol in the presence of triphenylphosphine and diethyl azodicarboxylate, by the method described in example 14(C), to provide 4-((2,2-dimethoxy)ethyl)-1-(7-(2,6,6-trimethyl-1 -cyclohexen-1-yl)heptyloxy)benzene as a yellow oil (1.08g, 83%) after chromatography with 1:1 dichloromethane-hexane. This is condensed with glyoxylic acid by the method of example 2, to provide the title compound, mp 78°–80° after recrystallization from dichloromethane-hexane.

Example 28

5-Hydroxy-4-(4-( 1-oxoundec-10-en-1-yl)phenyl)-2(5H)-furanone

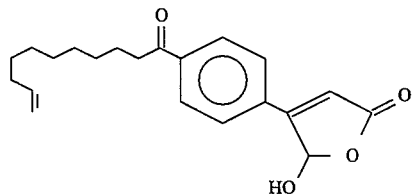

1-Bromo-4-(2-methoxyethenyl)benzene is prepared from 4-bromobenzaldehyde by the method of example 1(A). N-methoxy-N-methyl-10-undecenamide is prepared from the commercially available acid chloride and N,O-dimethylhydroxylamine in the usual fashion and obtained as a yellow oil after vacuum distillation.

To a solution of 1-bromo-(2-methoxyethenyl)benzene (2.13 g) in THF (20 ml) at −78° is added dropwise a 2.5M solution of n-butyllithium in hexane (4.2 ml). The temperature is not allowed to rise above -55°. After 90 min, a solution of N-methoxy-N-methyl-10-undecenamide (2.3 g) in THF (5 ml) is added dropwise, and the mixture stirred an additional 60 min at −78°. The mixture is not allowed to warm, but is immediately quenched by the addition of 10% aqueous citric acid. The mixture is extracted with dichloromethane, and the extracts are dried, filtered, and concentrated. The crude product is chromatographed with 1:1 dichloromethanehexane, to provide 1-(4-(2-methoxyethenyl)phenyl)-10-undecen-1-one as a colorless solid.

By the method of example 1, this is converted to the title compound, obtained as a colorless solid, mp 94°–95° after chromatography and recrystallization from hexane-ethyl acetate.

Example 29

5-Hydroxy-4-(4-(2-naphthoyl)phenyl)-2(5H)-furanone

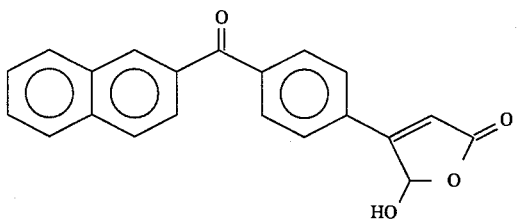

By the method of example 28, beginning with 2-naphthoyl chloride, the title compound is prepared, and is obtained as a yellow solid, mp 190°–191° after recrystallization from hexane-ethyl acetate.

Example 30

(E)-5-Hydroxy-4-(4-(3-(2-naphthyl)-1-oxo-2-propenyl)phenyl)-2(5H)-furanone

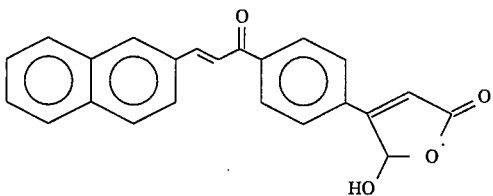

By the method of example 28, beginning with 3-(2-naphthyl)propenoyl chloride, the title compound is prepared, and is obtained as a yellow solid, mp 218°–220° after recrystallization from aqueous ethanol.

Example 31

5-Hydroxy-4-(4-(2-fluorobenzoyl)phenyl)-2(5H)-furanone

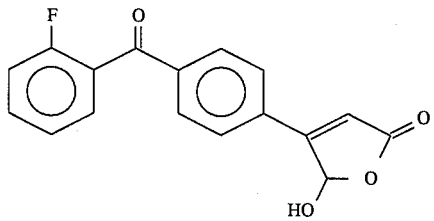

By the method of example 28, beginning with 2-fluorobenzoyl chloride, the title compound is prepared, and is obtained as a yellow solid, mp 177°–178° after recrystallization from aqueous ethanol.

Example 32

5-Hydroxy-4-(4-octanoylphenyl)-2(5H)-furanone

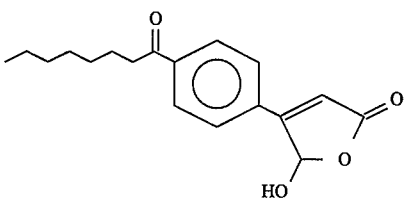

By the method of example 28, beginning with octanoyl chloride, the title compound is prepared, and is obtained as a colorless solid, mp 91°–92° after recrystallization from hexane-dichloromethane.

Example 33

(Z)-5-Hydroxy-4-(4-(2-phenylethenyl)phenyl)-2(5H)-furanone

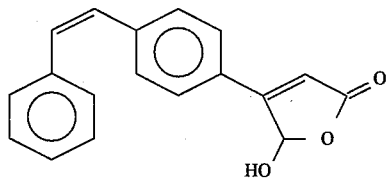

By the method of example 28, 1-bromo-4-(2-methoxyethenyl)benzene is prepared, lithiated, and reacted with dimethylformamide to provide 4-(2-methoxyethenyl) benzaldehyde as a yellow oil after chromatography. This material is converted to 1-(2-phenylethenyl)-4-(2-methoxyethenyl)benzene by Wittig reaction with benzyl triphenylphosphonium chloride, using the conditions described in example 1 (A). The material is obtained as a mixture of all four possible (E) and (Z) stereoisomers.

This enol ether (1.00 g) is dissolved in acetonitrile (85 ml), and sodium iodide (0.64 g) is added. Once the sodium iodide has dissolved, chlorotrimethylsilane (0.54 ml) is added, and the reaction mixture is stirred for ten minutes. The mixture is diluted with ether (300 ml), washed with 0.5N sodium thiosulfate, dried, filtered, and concentrated to provide crude 2-(4-(2-phenylethenyl)phenyl)acetaldehyde (1.0 g) as a pale yellow solid. The material, a mixture of (E) and (Z) isomers, is used immediately for the next step.

By the method of example 1 (C), this aldehyde is condensed with glyoxylic acid to provide a mixture of the title compound and the corresponding (E) isomer. Chromatography with 7% ethyl acetate in dichloromethane provides the title compound as a colorless solid, mp 128°–129° after recrystallization from hexane-ethyl acetate, as the first-eluting isomer.

Example 34

(E)-5-Hydroxy-4-(4-(2-phenylethenyl)phenyl)-2(5H)-furanone

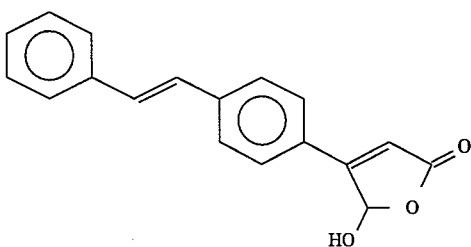

The title compound is isolated as the later-eluting isomer during the preparation of example 33, as a pale yellow solid, mp 233°–235° after recrystallization from hexane-ethyl acetate.

Example 35

(E)-5-Hydroxy-4-(4-(1-octenyl)phenyl)-2(5H)-furanone

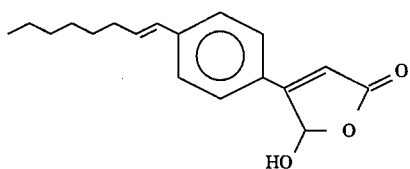

By the method of example 28, 1-bromo-4-(2-methoxyethenyl)benzene is prepared, lithiated, and reacted with octanal to provide 1-(4-(2-methoxyethenyl)phenyl)-1-octanol as a yellow oil after chromatography. The hydroxyl group is protected as the t-butyldimethylsilyl ether in the usual fashion, and the enol ether is then cleaved with chlorotrimethylsilane and sodium iodide as described in example 33. The resulting aryl acetaldehyde is obtained as an oil, and is immediately condensed with glyoxylic acid, by the method described in example 1(C). Under the reaction conditions, the silyl ether is simultaneously eliminated, and chromatography provides the title compound as a tan solid, mp 98°–99° after trituration with hot hexane.

Example 36

(E)-5-Hydroxy-4-(4-(4-phenyl-1-butenyl)phenyl)-2(5H)-furanone

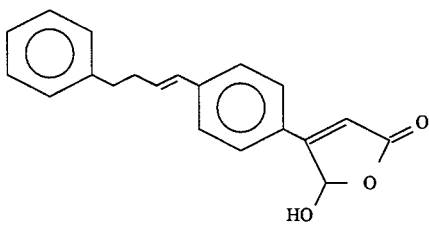

Using the conditions in example 1(A), (3-phenylpropyl)triphenylphosphonium bromide and methyl 4-formylbenzoate are condensed, providing methyl (E)-4-(4-phenyl-1-butenyl)benzoate as a colorless oil after chromatographic separation from the later-eluting (Z) isomer. This is reduced with lithium aluminum hydride in THF in the usual fashion to provide (E)-4-(4-phenyl-1-butenyl)phenylmethanol as a colorless oil. Oxidation with pyridinium dichromate in the usual fashion provides (E)-4-(4-phenyl-1-butenyl)benzaldehyde as a colorless oil after chromatography.

By the methods described in example 1, this benzaldehyde is chain-extended and condensed with glyoxylic acid to provide the title compound as a colorless solid, mp 116°–117° after recrystallization from hexane-ethyl acetate.

Example 37

5-Hydroxy-4-(4-((1-ethenylhexyl)oxy)phenyl)-2(5H)-furanone

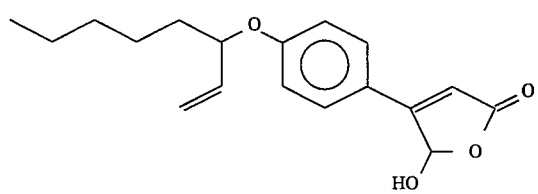

By the method of example 13, 4-hydroxybenzaldehyde and 1-nonen-3-ol are coupled under Mitsunobu conditions, producing 4-((1-ethenylhexyl)oxy)benzaldehyde. By the methods described in example 1, this benzaldehyde is chain-extended and condensed with glyoxylic acid to provide the title compound as a colorless oil after chromatography, which solidifies on standing giving a colorless solid, mp 46°–50°.

Example 38

(E)-5-Hydroxy-4-(4-hydroxy-3-(2-octenyl)phenyl)-2(5H)-furanone

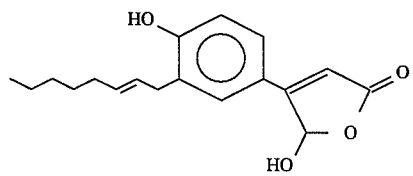

The 4-((1-ethenylhexyl)oxy)benzaldehyde prepared in example 37 is heated to 220° under nitrogen to effect a Claisen rearrangement. After 3 hours, the material is cooled to room temperature and chromatographed with 1% ether in dichloromethane, providing (E)-4-hydroxy-3-(2-octenyl)benzaldehyde as a colorless oil in 65% yield. The phenol group is protected in the usual fashion as a t-butyldimethylsilyl ether, and the aldehyde is then chain-extended and condensed with glyoxylic acid by the methods of example 1. The silyl ether is hydrolyzed in the course of the enol ether hydrolysis, and the title compound is obtained as a colorless solid, mp 136°–137° after recrystallization from hexane-ethyl acetate.

Example 39

(E)-5-Hydroxy-4-(4-((1-methyl-3-(2,6,6-trimethyl-1-cyclohexen-1-yl)propyl)oxy)phenyl)-2(5H)-furanone

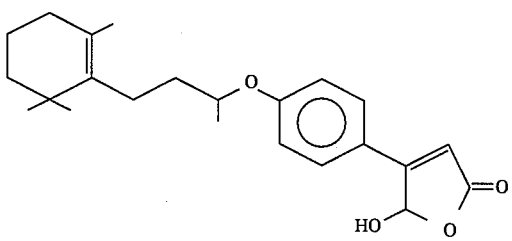

Dihydro-beta-ionone (*J. Am. Chem. Soc.*, 108, 7314 (1986)) is reduced with sodium borohydride in ethanol in the usual fashion to provide 4-(2,6,6-trimethyl-1-cyclohexen-1-yl)-2-butanol as a colorless oil. This is coupled with 4-hydroxybenzaldehyde by the method of example 13, and the resulting aldehyde is chain-extended and condensed with glyoxylic acid by the methods of example 1. The title compound is obtained as a colorless solid, mp 99°–101° after recrystallization from hexane-chloroform

Example 40

(Z,Z)-5-Hydroxy-4-((3-(octadeca-9,12-dienyl)oxy)phenyl)-2(5H)-furanone

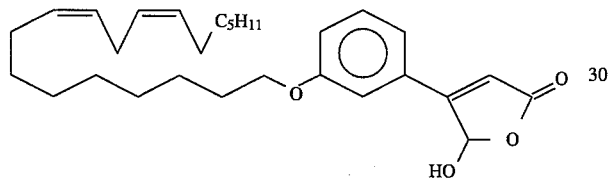

Linoleic acid ethyl ester is reduced in the usual fashion with lithium aluminum hydride in ether. The resulting alcohol is converted into the methanesulfonate ester with methanesulfonyl chloride in pyridine, and 3-hydroxybenzaldehyde is alkylated with this methanesulfonate in the presence of sodium hydride in DMF, by the method described in example 1(A). Chain extension and reaction with glyoxylic acid are carried out as in example 1, providing the title compound as a waxy white solid, mp 30°–35° after chromatography.

Example 41

5-Hydroxy-4-(3-hydroxy-4-(2-propenyl)phenyl)-2(5H)-furanone

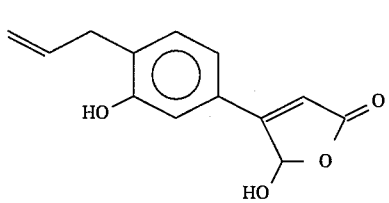

1-(2,2-Dimethoxyethyl)-3-(2-propenyloxy)benzene (an intermediate in the preparation of example 11) is heated to 200° under nitrogen for three hours to effect a Claisen rearrangement. The product is purified by chromatography to provide 5-(2,2-dimethoxyethyl)-2-(2-propenyl)phenol as a colorless oil in 22% yield. This acetal is hydrolyzed and condensed with glyoxylic acid by the methods of example 1 to provide the title compound as a pale yellow solid, mp 146°–147° after recrystallization from dichloromethane.

Example 42

5-Hydroxy-4-phenyl-2(5H)-furanone

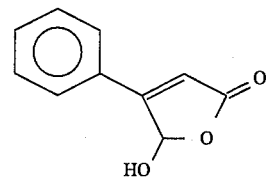

This material is prepared from phenylacetaldehyde by the method of example 1(C) and is obtained as a colorless solid, mp 158°–159°, (lit. mp 159°, *J. Org. Chem.*, 46, 4889 (1981)) after recrystallization from chloroform.

Example 43

5-Hydroxy-4-(3-phenoxyphenyl)-2(5H)-furanone

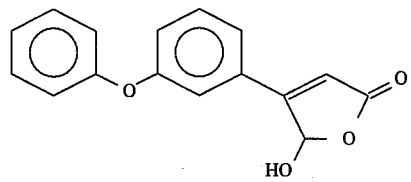

This material is prepared from 3-phenoxybenzaldehyde by the methods of example 1 and is obtained as a pale yellow solid, mp 138°–139° after recrystallization from hexane-chloroform.

Example 44

5-Hydroxy-4-(4-((4-(2-phenylethynyl)phenyl)methoxy)phenyl)-2(5H)-furanone

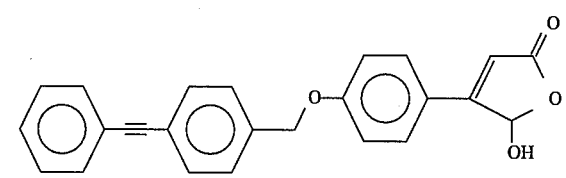

4-Hydroxybenzaldehyde is alkylated with 4-(2-phenylethynyl)benzyl bromide, and chain-extended and condensed with glyoxylic acid, by the methods of example 2. The product is obtained as a pale yellow solid, mp 208°–210° after recrystallization from ethyl acetate.

Example 45

5-Hydroxy-4-(4-(octylaminosulfonyl)phenyl)-2(5H)-furanone

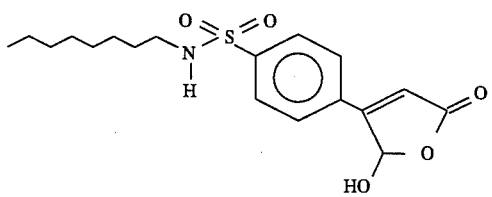

4-(Octylaminosulfonyl)benzoic acid is prepared in the usual way from octylamine and 4-(chlorosulfonyl)benzoic acid. This material is reduced with lithium aluminum hydride in THF in the usual fashion, and purified by chromatography with 1:3 ethyl acetate-dichloromethane to provide 4-(octylaminosulfonyl)benzyl alcohol as a colorless solid in 54% yield. Swern oxidation (DMSO-oxalyl chloride, dichloromethane) of this material provides 4-(octylaminosulfonyl)benzaldehyde as a colorless solid after chromatography. By the method of example 1(A), but using two equivalents of the phosphonium ylide, the aldehyde is chain-extended and converted to the dimethyl acetal, and by the method of example 2 this is condensed with glyoxylic acid to provide the title compound as a colorless solid, mp 223°–224° after recrystallization from ethyl acetate.

Example 46

5-Hydroxy-4-(4-(trifluoromethanesulfonoxy)phenyl)-2(5H)-furanone

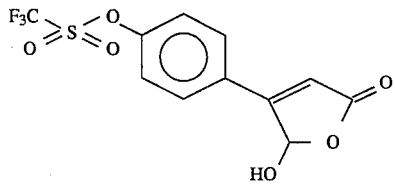

To a solution of 4-hydroxybenzaldehyde (12.3 g), triethylamine (16.3 ml), and 4-(dimethylamino)pyridine (DMAP) (1.86 g) in dichloromethane (170 ml), cooled to −10°, is added trifluoromethanesulfonic anhydride (17.0 ml) dropwise and with stirring. After 30 min the mixture is concentrated and the residue partitioned between water and ether. The ether layer is washed successively with 1.0N hydrochloric acid and 1.0N sodium bicarbonate solutions, then evaporated. The residue is chromatographed with dichloromethane, providing 4-(trifluoromethanesulfonoxy)benzaldehyde as a pale yellow oil (21.4 g, 84%). This material is converted into the title compound by the method of example 2, and is obtained as a colorless solid, mp 163°–164°, after recrystallization from hexane-ethyl acetate.

Example 47

5-Hydroxy-4-(3,5-bis(1-methylethyl)-4-hydroxyphenyl)-2(5H)-furanone

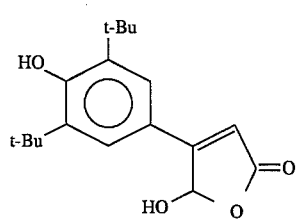

3,5-bis(1-methylethyl)-4-hydroxybenzaldehyde is acetylated with acetic anhydride in refluxing 1,2-dichloroethane, in the presence of DMAP, to provide 4-acetoxy-3,5-Bis(1-methylethyl)benzaldehyde. This material is converted by the method of example 2 into the title compound, obtained as a white solid, mp 95°–97° after recrystallization from hexane.

Example 48

5-Hydroxy-4-(4-((2-(3,4-dimethoxyphenyl)ethyl)aminocarbonyl)phenyl)-2(5H)-furanone

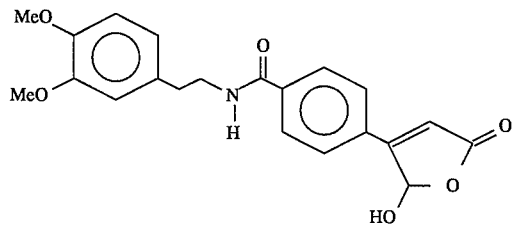

1-Bromo-4-(2-methoxyethenyl)benzene is prepared from 4-bromobenzaldehyde by the method of example 1(A). To a solution of this bromide (2.13 g) in THF (20 ml) at −70° is added a 2.5M solution of n-butyllithium in hexane (4.2 ml). The mixture is stirred at this temperature for 90 min (a precipitate is formed), and a solution of 2-(3,4-dimethoxyphenyl)ethyl isocyanate (2.18 g) in 5 ml THF is added dropwise. The mixture is stirred for 60 min, then quenched at this temperature with saturated ammonium chloride. The mixture is partitioned between ether and water, and the ether extract is dried, filtered, and chromatographed to provide N-(2-(3,4-dimethoxyphenyl)ethyl)-4-(2-methoxyethenyl)benzamide (mixture of E and Z isomers) as a white solid in 53% yield. This is converted into the title compound by the method of example 1 (B&C), and is obtained as a pale yellow solid, mp 135°–137°, after recrystallization from hexane-ethyl acetate.

Example 49

5-Hydroxy-4-(4-(phenylmethyl)phenyl)-2(5H)-furanone

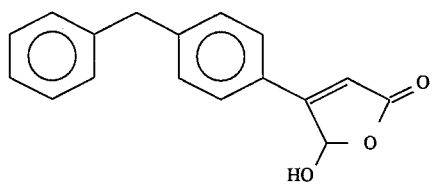

By the method of example 48, 1-bromo-4-(2-methoxyethenyl)benzene is lithiated and added to benzaldehyde. The crude product is acetylated with acetic anhydride in the presence of DMAP, providing alpha-(4-(2-methoxyethenyl)phenyl)benzyl acetate as a colorless oil. This ester (1.76 g) is treated with methanesulfonic acid (0.5 ml) in methanol (25 ml) at 50° for 16 hr. The acetoxy group and the enol ether are both solvolyzed in this reaction. The mixture is cooled, poured into saturated aqueous sodium bicarbonate, and extracted with three portions of ether, which are dried and evaporated to leave 1-(2,2-dimethoxyethyl)-4 -((methoxy)(phenyl)methyl)benzene as a colorless oil (1.62 g). The methoxy group is hydrogenolyzed by dissolving this material in ethyl acetate (100 ml), and shaking with 10% Pd/C under 50 psi hydrogen for 60 hr. Filtration and evaporation provide 1-(2,2-dimethoxyethyl)-4-(phenylmethyl)benzene as a colorless oil (1.46 g). By the method of example 1(B&C), this is converted into the title compound, which is obtained as a pale yellow solid, mp 148°–150° after recrystallization from hexaneethyl acetate.

Example 50

5-Hydroxy-4-(4-(2-naphthyloxy)phenyl)-2(5H)-furanone

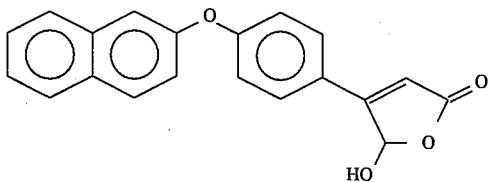

To a solution of 2-naphthol (14.4 g) in DMF (100 ml) is added sodium hydride (4.2 g of 60% dispersion). When gas evolution ceases, 4-fluorobenzaldehyde (11.5 ml) is added, and the reaction mixture is stirred at 130° for 48 hr. The mixture is cooled, poured onto crushed ice, and the product extracted with ether. Chromatography of the concentrated extract with 3:2 dichloromethane-hexane provides 4-(2-naphthyloxy)benzaldehyde as a pale yellow solid (10.25 g, 41%).

By the methods of example 1, this is converted into the title compound, which is obtained as a colorless solid, mp 175°–176° after recrystallization from hexane-ethyl acetate.

Example 51

5-Hydroxy-4-(4-(2-hydroxy-3-(2-naphthyloxy)propyl)phenyl)-2(5H)-furanone

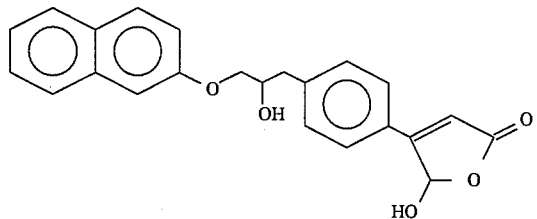

By the method of example 48, 1-bromo-4-(2-methoxyethenyl)benzene (2.13 g) is lithiated and reacted with (2-naphthyloxymethyl)oxirane (2.0 g). The reaction mixture is allowed to warm to room temperature and stirred for 48 hr before quenching with saturated ammonium chloride. The product is extracted with ether, and the extract is dried and concentrated to leave 1-(2-hydroxy-3-(2 -naphthyloxy)propyl)-4-(2-methoxyethenyl)benzene as a yellow oil (1.93 g). By the methods of example 1, this is converted into the title compound, which is obtained as a colorless solid, mp 175°–178° after recrystallization from hexane-ethyl acetate. This material is racemic at the propyl carbinol carbon, but substitution of a chiral form of the starting oxirane provides the title compound in chiral form.

Example 52

5-Hydroxy-4-(4-(2-naphthyloxymethyl)phenyl)-2(5H)-furanone

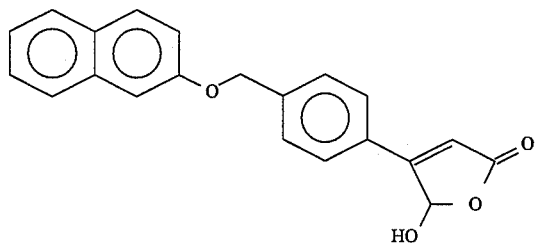

To a solution of 2-naphthol (26 g) in DMF (300 ml) is added sodium hydride (7.2 g of 60% dispersion). When gas evolution ceases, methyl 4-(chloromethyl)benzoate (32.9 g) and sodium iodide (10 g) are added, and the reaction mixture is stirred at 140° for 3 hr, and at 90° for an additional 18 hr. The mixture is cooled, poured into 2000 ml ice water, and the product extracted with 1:1 ether-hexane. The extracts are dried, filtered, and concentrated, providing methyl 4-(2-naphthyloxymethyl)benzoate as a tan solid (42.8 g, 91%). The ester is reduced with lithium aluminum hydride in THF in the usual fashion, and the resulting benzyl alcohol is converted by Swern oxidation (oxalyl chloride /DMSO) to 4-(2-naphthyloxymethyl)benzaldehyde. By the method of example 1, this is converted to the title compound, obtained as a pale yellow solid, mp. 213°–215° after recrystallization from hexane-ethyl acetate.

Example 53

5-Hydroxy-4-(4-(3,3-dimethyl-1-butynyl)phenyl)-2(5H)-furanone

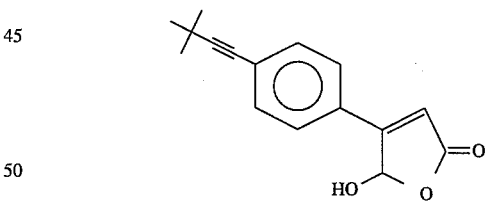

(A) A mixture of 4-bromobenzaldehyde (3.7 g), triphenylphosphine (0.32 g), palladium(II) acetate (135 mg), and 3,3-dimethyl-1-butyne (4 ml) in triethylamine (20 ml) is thoroughly purged with nitrogen, then heated to 100° in a sealed tube under nitrogen for 2 hr. The mixture is cooled, and the precipitated triethylamine hydrobromide is removed by filtration. The filtrate is concentrated, and the residue dissolved in 3:1 dichloromethane-hexane and filtered through a 2-cm pad of silica gel. The filtrate is concentrated and vacuum-distilled to provide 4-(3,3-dimethyl-1-butynyl)benzaldehyde as a pale yellow solid (3.25 g, 86%).

(B) By the methods of example 1, this is converted into the title compound, obtained as a colorless solid, mp. 174°–175° after recrystallization from hexanedichloromethane.

Example 54

5-Hydroxy-4-(4-(1-octynyl)phenyl)-2(5H)-furanone

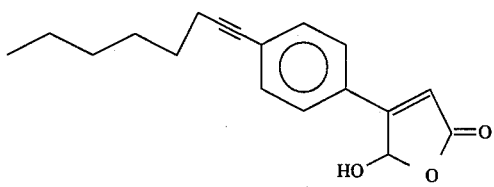

By the method of example 53(A), 4-bromobenzaldehyde is coupled with (trimethylsilyl)acetylene to provide 4-(2-(trimethylsilyl)ethynyl)benzaldehyde as a pale yellow solid after sublimation in vacuo. This material (5.8 g) is desilylated by stirring with potassium carbonate (0.4 g) in methanol (20 ml) for two hours. The solution is evaporated, and the product dissolved in methylene chloride, washed with water, dried, and concentrated to provide 4-ethynylbenzaldehyde as a yellow solid (3.45 g, 90%). By the Wittig reaction of example 1(A), this is chain-extended to provide 1-ethynyl-4-(2-methoxyethenyl)benzene, obtained as a colorless oil after distillation in vacuo (3.10 g, 77%).

This material (2.18 g) is dissolved in THF (15 ml), cooled to −78°, and n-butyllithium (5.8 ml of 2.5M solution in hexane) is added dropwise. After 15 min, 1-iodohexane (2.16 ml) is added. The mixture is stirred for 60 min, and allowed to warm to room temperature. The mixture is quenched with saturated ammonium chloride, and the product extracted with hexane. The extracts are concentrated and chromatographed, providing 1-(2-methoxyethenyl)-4-(1-octynyl)benzene as a yellow oil (2.88 g, 86%).

By the methods of example 1 (B&C), this is converted into the title compound, obtained as a pale yellow solid, mp 88°–90° after recrystallization from dichloromethane-ethyl acetate.

Example 55

5-Hydroxy-4-(4-(2-phenylethynyl)phenyl)-2(5H)-furanone

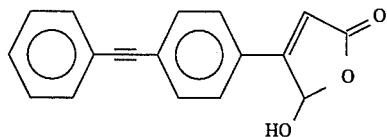

By the method of example 53(A), but using bis(triphenylphosphine)palladium(II) acetate as catalyst (3 mol %), phenylacetylene and 4-bromobenzaldehyde are coupled to give 4-(2-phenylethynyl)benzaldehyde in 70% yield after distillation. By the methods of example 1, this is converted into the title compound, obtained as a colorless solid, mp 190°–191° after recrystallization from hexane-ethyl acetate.

Example 56

5-Hydroxy-4-(4-(2-(2-naphthyl)ethynyl)phenyl)-2(5H)-furanone

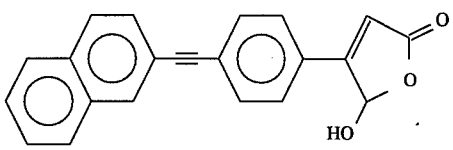

4-(Trifluoromethanesulfonoxy)benzaldehyde is prepared by the method of example 46. By the method of example 53(A), this is coupled with 2-ethynylnaphthalene to provide 4-(2-(2-naphthyl)ethynyl)benzaldehyde, which is converted to the title compound by the method of example 2. The product is obtained as a pale yellow solid, mp 232°–234° after recrystallization from ethyl acetate.

Example 57

5-Hydroxy-4-(4-(2-(1-naphthyl)ethynyl)phenyl)-2(5H)-furanone

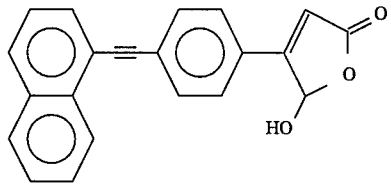

By the method of example 56, 1-ethynylnaphthalene is converted to the title compound, a yellow solid, mp 194°–196° after recrystallization from ethyl acetate.

Example 58

5-Hydroxy-4-(4-(2-(4-(trifluoromethyl)phenyl)ethynyl)phenyl)-2(5H)-furanone

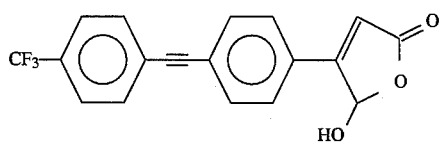

1-Ethynyl-4-(2-methoxyethenyl)benzene is prepared as in example 54. This material is converted into the dimethyl acetal with methanol-methanesulfonic acid, by the method of example 1 (B), providing 1-(2,2,-dimethoxyethyl)-4-ethynylbenzene as a colorless oil after chromatography. By the method of example 53(A), this material is coupled with 1-bromo-4-(trifluoromethyl)benzene to provide 1-(2,2,-dimethoxyethyl)-4-(2-(4-(trifluoromethyl)phenyl)ethynyl)benzene as a pale yellow oil. This is converted to the title compound by the method of example 2. The material is obtained as a colorless solid, mp 219°–220° after recrystallization from ethyl acetate.

Example 59

5-Hydroxy-4-(4-(2-(3-nitrophenyl)ethynyl)phenyl)-2(5H)-furanone

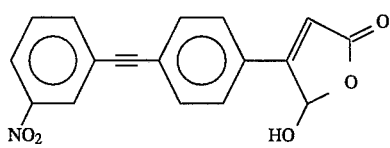

By the method of example 55, (3-nitrophenyl)acetylene is converted into the title compound, obtained as a yellow solid, mp 193°–194° after recrystallization from ethyl acetate.

Example 60

5-Hydroxy-4-(4-(2-(4-nitrophenyl)ethynyl)phenyl)-2(5H)-furanone

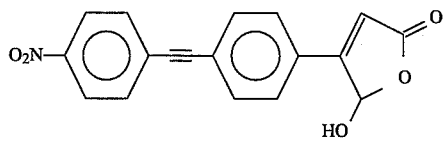

By the method of example 55, (4-nitrophenyl)acetylene is converted into the title compound, obtained as a yellow solid, mp 229°–231° after recrystallization from ethyl acetate.

Example 61

5-Hydroxy-4-(4-(2-(4-methoxyphenyl)ethynyl)phenyl)-2(5H)-furanone

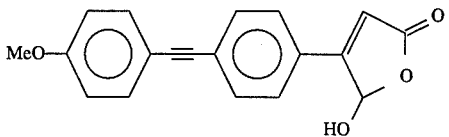

By the method of example 55, (4-methoxyphenyl)acetylene is converted into the title compound, obtained as a yellow solid, mp 207°–208° after recrystallization from aqueous ethanol.

Example 62

5-Hydroxy-4-(4-(2-Coenzo[b]thiophen-2-yl)ethynyl)phenyl)-2(5H)-furanone

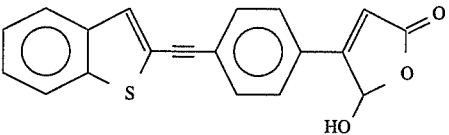

2-Iodobenzo[b]thiophene (*Tetrahedron,* 40, 2773 (1984)) is coupled with 1-(2,2,-dimethoxyethyl)-4-ethynylbenzene, and the product converted into the title compound, by the method of example 58. The material is obtained as a yellow solid, mp 250°–252°, after recrystallization from methanol-ethyl acetate.

Example 63

5-Hydroxy-4-(3-(2-phenylethynyl)phenyl)-2(5H)-furanone

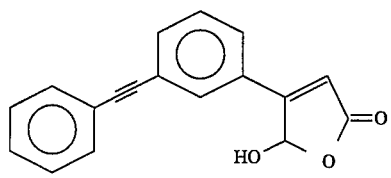

By the method of example 55, but starting with 3-bromobenzaldehyde, the title compound is prepared. It is obtained as a colorless solid, mp 159°–161°, after recrystallization from hexane-ethyl acetate.

Example 64

5-Hydroxy-4-(4-(octyloxy)phenylthio)-2(5H)-furanone

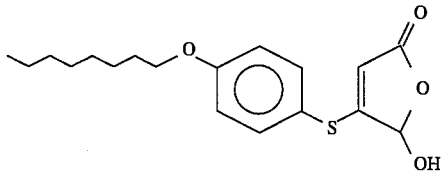

To a solution of 4-mercaptophenol (3.81 g) in DMF (80 ml) is added potassium carbonate (8.3 g) and 1-bromo-2,2-dimethoxyethane (3.55 g). The mixture is stirred at 70° under nitrogen for 2 hr, then cooled and poured into 0.1N citric acid (600 ml). The product is extracted with ether, and the ether extracts are concentrated and distilled in vacuo (140°–145°, 0.01 torr), to provide 4-((2,2-dimethoxyethyl)thio)phenol as a pale yellow viscous oil (5.21 g, 81%).

This phenol is alkylated again by the same method, but using sodium hydride and 1-bromooctane, to provide 1-((2,2-dimethoxyethyl)thio)-4-(octyloxy)benzene as a colorless oil after chromatography (87% yield). By the method of example 2, this is converted into the title compound, obtained as a pale yellow solid, mp 70°–72° after recrystallization from hexane-dichloromethane.

Example 65

5-Hydroxy-4-(4-(tridecyloxy)phenylthio)-2(5H)-furanone

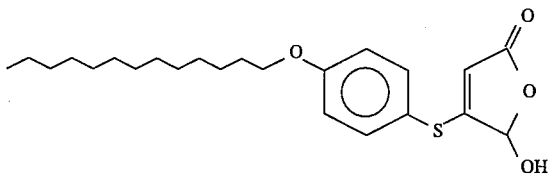

By the method of example 64, but using 1-bromotridecane, the title compound is prepared, and obtained as a colorless solid, mp 65°–66° after recrystallization from hexane.

Example 66

5-Hydroxy-4-(4-(pentyloxy)phenylthio)-2(5H)-furanone

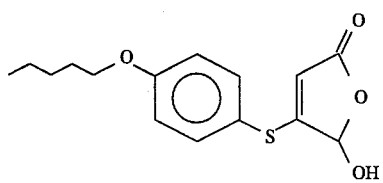

By the method of example 64, but using 1-bromopentane, the title compound is prepared, and obtained as a light tan solid, mp 79°–81° after recrystallization from hexane.

Example 67

(E)-5-Hydroxy-4-(4-(2-methyl-4-(2,6,6-trimethyl-1-cyclohexen-1-yl)-2 -butenyloxy)phenylthio)-2(5H)-furanone

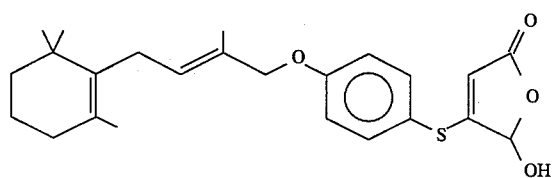

By the method of example 13, 4-((2,2-dimethoxyethyl)thio)phenol (example 64) and (E)-2-methyl-4-(2,6,6-trimethyl-1-cyclohexen-1-yl)-2-butenol (*Chem. Abstr.*, 94, 65904 h) are coupled in the presence of triphenylphosphine and diethyl azodicarboxylate to provide (E)-1-((2,2-dimethoxyethyl)thio)-4-(2-methyl-4-(2,6,6 -trimethyl-1-cyclohexen-1-yl)-2-butenyloxy)benzene as a colorless oil after chromatography (85% yield).

By the method of example 2, this is converted into the title compound, obtained as a colorless solid, mp 119°–121°, after recrystallization from hexane.

Example 68

5-Hydroxy-4-( (4-bromophenyl)thio)-2(5H)-furanone

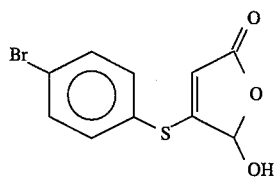

By the method of example 64, 4-bromothiophenol is alkylated with 1-bromo-2,2-dimethoxyethane, and converted into the title compound, isolated as a colorless solid, mp 154°–156° after recrystallization from hexane-ethyl acetate.

Example 69

5-Hydroxy-4-(6-octyloxy-3-pyridyl)-2(5H)-furanone

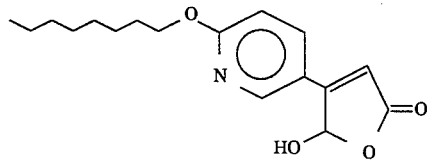

A mixture of 6-chloropyridine-3-carboxamide (14 g), phosphorous oxychloride (35 ml) and chloroform (120 ml) is refluxed for 2 hr, cooled, and concentrated. The residue is stirred with water and the resulting precipitate is collected and recrystallized from ethanol to provide 10.3 g (83 %) of 6-chloropyridine-3-carbonitrile. This nitrile (2.77 g) is added to a solution of sodium octanolate (prepared from 1-octanol (2.78 g) and sodium hydride (0.88g of 60% dispersion) in DMF (20 ml)). After 30 min at room temperature, the mixture is poured into water, and the product extracted with ether. The extracts are concentrated and chromatographed with 2:3 hexane-dichloromethane, to provide 6 -(octyloxy)pyridine-3-carbonitrile as a colorless oil (3.7 g, 80%). This nitrile is dissolved in toluene (15 ml), cooled to –20°, and diisobutylaluminum hydride (12.5 ml of 1.5M solution in toluene) is added dropwise. After an hour, the mixture is poured into 1.0N hydrochloric acid and the product extracted with ether. The extracts are dried, filtered, and concentrated to leave 6-(octyloxy)pyridine-3-carboxaldehyde (2.36 g) as a yellow oil.

By the method of example 2, this material is converted into the title compound, isolated as a colorless solid, mp 94°–95° after recrystallization from ethyl acetate.

Example 70

5-Hydroxy-4-(2-(octylthio)-4-thiazolyl)-2(5H)-furanone

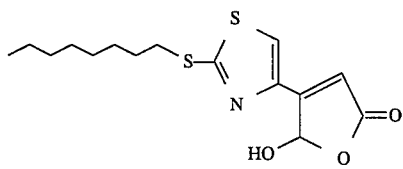

To a solution of 2-mercaptothiazole-4-carboxylic acid ethyl ester (Zhelyazkov, L.; Todorova, N.; Manolova, P. *Tr. Nauchnoizsled. Khim.-Farm. Inst.*, 9, 59–67 (1974); *Chem. Abstr.*, 83, 58706 q) (3.0 g) in DMF (20 ml) is added sodium hydride (0.70 g of 60% dispersion). After 10 min, 1-bromooctane (3.0 ml) is added, and the mixture is stirred at 60° for 30 min. The mixture is poured into water and extracted with ether, and the extracts are dried, filtered, and concentrated. The residue is recrystallized from hexane to provide 2-(octylthio)thiazole-4-carboxylic acid ethyl ester as a colorless solid (3.7 g, 78%). This material is reduced in the usual fashion with lithium aluminum hydride in THF, providing 2-(octylthio)thiazole-4-methanol (2.12 g, 67%) as a colorless oil after chromatography. This is combined with DDQ (1.8 g) in 1,4-dioxane (25 ml) and stirred for 48 hr at room temperature. The reaction mixture is filtered, and the filtrate is concentrated and chromatographed with dichloromethane to provide 2-(octylthio)thiazole-4-carboxaldehyde as a tan solid (1.67 g, 81%).

By the method of example 2, this aldehyde is converted into the title compound, isolated as a colorless solid, mp 89°–91 ° after recrystallization from hexane.

Example 71

5-Hydroxy-4-methyl-2(5H)-furanone

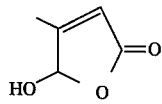

To a mixture of morpholine hydrochloride (4.56 g) and glyoxylic acid hydrate (4.6 g) in 1,4-dioxane (50 ml) is added sufficient water to make a homogeneous solution. To this solution is added 1,1-diethoxypropane (6.61 g), and the mixture is heated to reflux. The 1,1-diethoxypropane dissolves within a few minutes. The mixture is stirred at reflux for 12 hr, cooled, and concentrated to a viscous gum. This is treated with ethyl acetate (50 ml), and the precipitate of morpholine hydrochloride is filtered. The filtrate is concentrated to a brown oil, which is stirred overnight with 0.1N hydrochloric acid in saturated aqueous sodium chloride (25 ml) to hydrolyze morpholine adducts. The mixture is extracted twice with ether, the ether extracts are washed once with saturated sodium chloride and concentrated, and the residue is distilled in vacuo, providing the title compound as a pale yellow, viscous oil (5.0 g), with NMR spectrum as reported by Pattenden and Weedon, *J. Chem. Soc. C*, 1984 (1968).

Example 72

5-Hydroxy-4-(2-octyloxy-3-pyridyl)-2(5H)-furanone

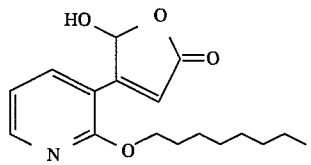

By the method of example 69, 2-chloropyridine-3-carbonitrile (*Can. J. Chem.*, 66(3), 420 (1988)) is converted into the title compound.

Example 73

5-Hydroxy-4-(4-octyloxy-3-pyridyl)-2(5H)-furanone

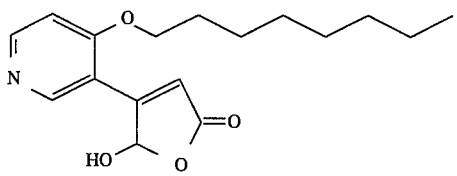

By the method of example 69, 4-chloropyridine-3-carbonitrile (*Chem. Pharm. Bull.*, 36(6), 2244 (1988)) is converted into the title compound.

Example 74

5-Hydroxy-4-(3-octyloxy-4-pyridyl)-2(5H)-furanone

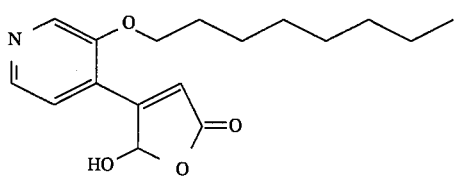

By the method of example 69, 3-chloropyridine-4-carbonitrile (*J. Heterocyclic Chem.*, 15(4), 683 (1978)) is converted into the title compound.

Example 75

5-Hydroxy-4-(5-octyloxy-2-pyridyl)-2(5H)-furanone

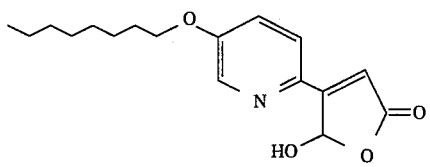

By the method of example 69, 5-chloropyridine-2-carbonitrile (*Chem. Pharm. Bull.*, 33(2), 565 (1985)) is converted into the title compound.

Example 76

5-Hydroxy-4-(2-(octyloxy)-4-thiazolyl)-2(5H)-furanone

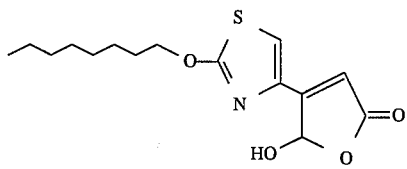

Ethyl 2-(octyloxy)-thiazole-4-carboxylate is prepared by the method described by R. Howe and L. Lee, U.S. Pat. No. 4,298,375. By the method of example 70, this ester is reduced and the resulting alcohol oxidized to provide 2(octyloxy)thiazole-4-carboxaldehyde. By the method of example 2 this is converted into the title compound.

B. ACTIVITY OF THE COMPOUNDS

The biochemical and biological activities of the compounds against phospholipase $A_2$ and TPA-induced topical inflammation are presented in Table 1.

The activity of the compounds of the invention against phospholipase $A_2$ is determined using a preparation of human platelet phospholipase $A_2$ with a specific activity of 180 nmol/min/mg as the enzyme source. Polypropylene 15-ml test tubes are utilized as the reaction vessels. All drug samples are run in duplicate, with "blank" and "control" (no test compound) groups run in triplicate. Gossypol is utilized as an internal standard and run at its $IC_{50}$ concentration of 1 μM. Test compounds are dissolved in DMSO, and diluted to a projected final concentration of either 50 or 10 μM in 550 μl HEPES buffer at pH 7.0. A 1:7 dilution of human platelet $PLA_2$ in HEPES buffer (5 μl) is added to each test tube, followed by gentle vortexing for 3 seconds. The reaction tubes containing drug, buffer, and enzyme are preincubated for 15 min at 37°, followed by the addition of 25 μl of $^{14}$C-oleate E. coli substrate. Details regarding this substrate may be found in a publication by S. Ghosh and R. Franson, *Biochem. Cell. Biol.*, 70, 43 (1992), and references therein.

The tubes are immediately vortexed at moderate speed for 3 sec, followed by a 60 min incubation at 37° in a shaking water bath. The reaction is stopped by the addition of 3 ml of a 1:2 chloroform-methanol mixture. Additional water (1.5 ml) and chloroform (1.0 ml) are added, followed by vortexing. The lower phase is removed with a polypropylene transfer pipette, and transferred to a 13×100 mm polypropylene test tube. The organic solvent is evaporated with a stream of nitrogen, the residue is redissolved in 30 μl of a 9:1 chloroform-methanol mixture, and the solution is spotted on a channeled polyester-backed silica gel TLC plate, such as those available under the trade name PE SIL G available from Whatman Inc, Clifton, N.J.

The plate is developed with an 80:20:1 mixture of petroleum ether-diethyl ether-acetic acid. Exposure of the plate to iodine vapor reveals the location of the fatty acids released by the enzyme, and the location of the starting phospholipids at the origin. The plate is scored above the origin, cut along the score with scissors, and the reactant (origin) and product portions of each channel are put into separate scintillation vials. To each vial is added a scintillation cocktail (15 ml), preferably that sold under the trademark ECOLUME by ICN Biomedicals, Irvine Calif. The vials are shaken vigorously for 5 sec, and the radioactive $^{14}$C in each vial is measured with a scintillation counter, which provides the counts-per-minute (cpm) for each sample. The obtained cpm values are corrected for the "blank" values.

The percentage of phospholipid hydrolyzed is calculated by the formula:

Phospholipid converted=100×cpm products / (cpm products+cpm reactants)

The inhibition of phospholipase A2 by the test compounds is expressed as a percent inhibition relative to the control group:

% Inhibition=100×(experimental % conversion / control % conversion)

The topical anti-inflammatory activity of the compounds is determined by measuring the degree of inhibition of TPA-induced inflammation in the mouse ear, using essentially the procedure of C. Van Arman, *Clin. Pharmacol. Ther.*, 16, 900 (1974). Male CD-1 mice are used at seven to nine weeks of age. 12-O-tetradecanoylphorbol acetate ( 1.0 μl in 20 μl of acetone) is dispensed onto the dorsum of the left ear of each mouse, and the right ear is left untreated. Ten mice so treated serve as the control group. In a single-dose experiment, an experimental group of ten mice is treated in the same way, except that 100 μl of the compound to be tested is incorporated into the TPA solution.

After five to six hours, the animals are sacrificed by $CO_2$ inhalation, the ears are removed, and 7 mm circular punch biopsies of are taken from each ear and weighed. The difference in biopsy weight between treated and untreated ears is determined, and the degree of anti-inflammatory activity is expressed in terms of the percent inhibition of ear weight increase relative to the control group. In multiple-dose experiments, varying amounts of the compound to be tested are applied along with the TPA and the results are expressed as the $ED_{50}$, the dose at which a 50% inhibition of weight gain is observed.

TABLE 1

Biological Activity of Compounds

| Example | Inhibition of PLA2 | | Inhibition of ear edema | |
|---|---|---|---|---|
| | % Inhibition @ 50 (*or 10) μM | $IC_{50}$ (μM) | % Inhibition @ 100 μg | $IC_{50}$ (μg) |
| 1 | 91 | 14 | 56 | 300 |
| 2 | *69 | 7.5 | | |
| 3 | 39 | | | |
| 4 | *71 | 5.4 | | |
| 5 | *58 | | | |
| 6 | *27 | | | |
| 7 | *67 | 9.4 | | |
| 8 | *21 | | | |
| 9 | *7 | | | |
| 10 | 17 | | | |
| 11 | 0 | | | |
| 12 | 47 | | 45 | |
| 13 | 73 | 22 | 0 | |
| 14 | 87 | | 4 | |
| 15 | 94 | | 49 | |
| 16 | 100 | 9 | 43 | 106 |
| 17 | 100 | 8 | 51 | 87 |
| 18 | 75 | | 70 | 28 |
| 19 | 98 | 5 | 20 | |
| 20 | 0 | | | |
| 21 | 0 | | | |
| 22 | *49 | | | |
| 23 | 78 | 8 | 56 | |
| 24 | 0 | | | |
| 25 | *40 | | | |
| 26 | *92 | | | |
| 27 | 67 | 1.4 | 35 | |
| 28 | 86 | 9 | 0 | |
| 29 | 59 | 50 | | |
| 30 | 92 | 7 | 66 | 80 |
| 31 | 6 | | | |
| 32 | 55 | | | |
| 33 | 23 | | | |
| 34 | 91 | 30 | 33 | |
| 35 | 100 | 5 | 30 | |
| 36 | 84 | 24 | 37 | |
| 37 | 93 | 20 | 34 | |
| 38 | 85 | 50 | 78 | 27 |
| 39 | 95 | 20 | 48 | 94 |
| 40 | 100 | 7 | 80 | |
| 41 | 0 | | 64 | |
| 42 | 9 | | 45 | |
| 43 | 30 | | 52 | |
| 44 | 90 | | 43 | |
| 45 | 13 | | | |
| 46 | 0 | | | |
| 47 | *2 | | | |
| 48 | 0 | | | |
| 49 | 5 | | | |
| 50 | 52 | 50 | | |
| 51 | 30 | | | |
| 52 | 51 | 50 | | |
| 53 | 53 | 42 | | |
| 54 | 100 | 5 | 9 | |
| 55 | 67 | 19 | 79 | 37 |
| 56 | 59 | | | |
| 57 | 69 | 8.4 | | |
| 58 | *24 | | | |
| 59 | *6 | | | |
| 60 | *11 | | | |
| 61 | 33 | | | |
| 62 | *33 | | | |
| 63 | *45 | | | |
| 64 | 96 | 5 | 48 | |
| 65 | *98 | | | |
| 66 | *48 | | | |
| 67 | 98 | 0.5 | | |
| 68 | 0 | | | |

TABLE 1-continued

| | Biological Activity of Compounds | | | |
|---|---|---|---|---|
| | Inhibition of PLA2 | | Inhibition of ear edema | |
| Example | % Inhibition @ 50 (*or 10) μM | IC$_{50}$ (μM) | % Inhibition @ 100 μg | IC$_{50}$ (μg) |
| 69 | 52 | | | |
| 70 | 70 | | | |

The above test results demonstrate the utility of the compounds of the invention for inhibiting PLA$_2$ and ear edema, thus demonstrating antiinflammatory activity.

D. FORMULATION OF THE COMPOUNDS OF THE INVENTION

The compounds of the invention may be administered by conventional routes: e.g., orally, parenterally, or topically, as appropriate to the disease being treated, preferably, orally or topically. The compounds may be formulated by admixture with such diluents, carriers, and excipients as are appropriate for the intended route of administration.

Pharmaceutical compositions containing compounds of the invention may comprise the compound of the present invention and a pharmaceutically acceptable carrier in either solid or liquid form. Solid form preparations include powders, tablets, dispersible granules, capsules, etc. The carrier may also be one or more substances which act as diluents, flavoring agents, solubilizers, lubricants, suspending agents, binders, or tablet disintegrating agents as well as encapsulating materials. Suitable carriers are magnesium carbonate, magnesium stearate, talc, lactose, sugar, peptin, dextrin, starch, methyl cellulose, sodium carboxyl methyl cellulose, and the like. Liquid form preparations include solutions which are suitable for oral or parenteral administration, or suspensions and emulsions suitable for oral administration.

Sterile water solutions of the active component or sterile solutions of the active components in solvents comprising water, ethanol, or propylene glycol are examples of liquid preparations suitable for parenteral administration. Sterile solutions may be prepared by dissolving the active component in the desired solvent system, then passing the resulting solution through a membrane filter to sterilize it, or alternatively, by dissolving the sterile compound in a previously sterilized solvent under sterile conditions. Solutions for oral administration can be prepared by dissolving the active compound in water, ethanol or propylene glycol and adding suitable flavorants, coloring agents, stabilizers and thickening agents as required. Aqueous suspensions for oral use can be made by dispersing the finely divided active component in water together with a viscous material such as a natural or synthetic gum, methyl cellulose, sodium carboxy methyl cellulose, and other suspending agents known to the pharmaceutical formulation art.

It is especially advantageous to formulate the aforementioned pharmaceutical compositions in unit dosage form for ease of administration and uniformity of dosage. The term "unit dosage form" as used herein refers to physically discrete units suitable as unit dosages, each unit containing a predetermined quantity of active ingredient calculated to produce the desired therapeutic effect in association with the required pharmaceutical carrier.

Various conventional techniques for preparing pharmaceutical compositions including solutions, suspensions, tablets or caplets can be employed, as would be known to those skilled in the art and as disclosed for example by Remington's *Pharmaceutical Sciences*, Mack Publishing Co., Part 8 Chapters 76–93, "Pharmaceutical Preparations and Their Manufacture", pp. 1409–1677 (1985).

In therapeutic use as antiinflammatory agents, the compounds utilized in the methods of this invention may be administered to a patient either orally or parenterally at dosage levels of from about 0.1 to 100 mg/kg per day, preferably about 1 to 10 mg/kg per day; and topically about 0.01 to 100 mg/cm$^2$, preferably about 0.1 to 10 mg/cm$^2$. The dosages, however, may be varied depending upon the results of specific clinical testing, the requirements of the patient, the weight and age of the patient, the severity of the condition being treated, and the compound being employed. Determination of optimum dosages for a particular situation is within the skill of the art.

The scope of the present invention is not limited by the description, examples and suggested uses described herein and modifications can be made without departing from the spirit of the invention. For example, additional medicaments or active components may be used in combination with the compounds of the invention. Further, the novel compounds of the invention may have other uses in addition to those described herein. For example, the compounds of the invention may be useful for treatment of cardiovascular disease states.

Applications of the compounds, compositions and methods of the present invention for medical or pharmaceutical uses can be accomplished by any clinical, medical, and pharmaceutical methods and techniques that are presently or prospectively known to those skilled in the art. Thus it is intended that the present invention cover any modifications and variations of this invention provided that they come within the scope of the appended claims and their equivalents.

What is claimed is:

1. A compound of formula:

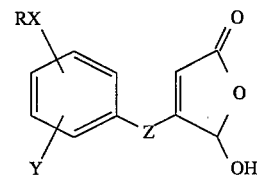

wherein

R contains from about five to about twenty carbon atoms and is selected from alkyl, acyl, cycloalkyl (C$_3$–C$_8$), aryl-alkyl, (cycloalkyl)alkyl, alkenyl, aryl-alkenyl, alkynyl, (cycloalkyl)alkynyl, (cycloalkyl)alkenyl, aryl-alkynyl or aryl groups wherein said alkyl, cycloalkyl, aryl-alkyl, (cycloalkyl)alkyl, alkenyl, aryl-alkenyl, alkynyl, (cycloalkyl)alkynyl, (cycloalkyl)alkenyl, aryl-alkynyl or aryl groups are unsubstituted or substituted by one or more lower alkyl groups(C$_1$–C$_8$), wherein said cycloalkyl groups contain 3–8 carbon atoms and include no or one or more double bonds, said aryl groups are selected from phenyl and naphthyl and are monocyclic or fused bicyclic, and said aryl groups are unsubstituted or substituted by one or more halogen, nitro, lower alkyl, lower alkylthio, perfluoroalkyl, hydroxy, or lower alkoxy groups(C$_1$–C$_8$);

X is oxygen, sulfur, SO$_2$, NH, N(lower alkyl), N(lower acyl), aminocarbonyl, carbonyl, carbonylamino, CH$_2$ or a carbon-carbon bond;

Y is hydrogen, halogen, lower alkyl, nitro, alkylthio, perfluoroalkyl, hydroxy, or lower alkoxy(C$_1$–C$_8$); and Z is sulfur or a carbon-carbon bond; and pharmaceutically acceptable salts thereof.

2. The compound according to claim 1 wherein RX is hydrophobic and non-polar.

3. The compound according to claim 1 wherein X is oxygen or sulfur.

4. The compound according to claim 1 wherein Y is hydrogen or halogen.

5. The compound according to claim 3 wherein Y is hydrogen or halogen.

6. The compound according to claim 1 wherein Z is sulfur.

7. The compound according to claim 1 wherein R is alkyl, aryl-alkyl, (cycloalkyl)alkyl, alkenyl, aryl-alkenyl or (cycloalkyl)alkenyl X is oxygen or sulfur; and Y is hydrogen or halogen.

8. The compound according to claim 1 wherein R is alkyl, aryl-alkyl, (cycloalkyl)alkyl, alkenyl, aryl-alkenyl or (cycloalkyl)alkenyl and Z is sulfur.

9. The compound according to claim 1 wherein R is alkenyl, aryl-alkenyl or (cycloalkyl)alkenyl.

10. The compound according to claim 1 wherein R is alkenyl or (cycloalkyl)alkenyl and Z is sulfur.

11. The compound according to claim 1 wherein the compound is:

5-Hydroxy-4-(4-(7-(2,6,6-trimethyl-1-cyclohexen-1-yl)heptyloxy)phenyl)-2(5H)-furanone;

(E)-5-Hydroxy-4-(4-hydroxy-3-(2-octenyl)phenyl)-2(5H)-furanone;

(Z,Z)-5-Hydroxy-4-((3-(octadeca-9,12-dienyl)oxy)phenyl)-2(5H)-furanone;

5-Hydroxy-4-(4-(2-phenylethynyl)phenyl)-2(5H)-furanone; or (E)-5-Hydroxy-4-(4-(2-methyl-4-(2,6,6-trimethyl-1-cyclohexen-1-yl)-2-butenyloxy)phenylthio)-2(5H)-furanone.

12. A pharmaceutical composition comprising a compound of claim 1 and one or more pharmaceutically acceptable excipients.

13. A method of treating a mammal having a disease characterized by the overproduction of arachidonic acid metabolites, said method comprising administering to said mammal a therapeutically effective amount of a material of claim 1.

14. The method of claim 13 wherein said disease is an inflammatory disease.

15. The method of claim 13 wherein said disease is an allergic condition.

16. The method of claim 13 wherein said disease is psoriasis.

17. The method of claim 13 wherein said material is applied topically.

18. A pharmaceutical composition comprising a compound of claim 1 and a pharmaceutically acceptable carrier.

* * * * *